United States Patent
Sartor et al.

(10) Patent No.: US 7,572,255 B2
(45) Date of Patent: Aug. 11, 2009

(54) GAS-ENHANCED SURGICAL INSTRUMENT

(75) Inventors: Joe D. Sartor, Longmont, CO (US);
Michael Hogan, Boulder, CO (US);
Gene H. Arts, Berthoud, CO (US);
Ronald J. Podhajsky, Boulder, CO (US); Arlan J. Reschke, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 639 days.

(21) Appl. No.: 11/229,814

(22) Filed: Sep. 19, 2005

(65) Prior Publication Data
US 2006/0052772 A1    Mar. 9, 2006

Related U.S. Application Data

(63) Continuation-in-part of application No. 11/048,577, filed on Feb. 1, 2005.

(60) Provisional application No. 60/541,326, filed on Feb. 3, 2004.

(51) Int. Cl.
*A61B 18/14* (2006.01)
(52) U.S. Cl. .............................. 606/41; 606/45; 606/49
(58) Field of Classification Search .................. 606/41, 606/46, 48–50
See application file for complete search history.

(56) References Cited

U.S. PATENT DOCUMENTS

| | | | |
|---|---|---|---|
| 2,708,933 A | 5/1955 | August | |
| 2,828,747 A | 4/1958 | August | |
| 3,434,476 A | 3/1969 | Shaw et al. | |
| 3,569,661 A | 3/1971 | Ebeling | |
| 3,692,973 A | 9/1972 | Oku et al. | |
| 3,699,967 A | 10/1972 | Anderson | |
| 3,832,513 A | 8/1974 | Klasson | |
| 3,838,242 A | 9/1974 | Goucher | |
| 3,903,891 A | 9/1975 | Brayshaw | |
| 3,970,088 A | 7/1976 | Morrison | |
| 3,987,795 A | 10/1976 | Morrison | |
| 3,991,764 A | 11/1976 | Incropera et al. | |
| 4,014,343 A | 3/1977 | Esty | |

(Continued)

FOREIGN PATENT DOCUMENTS

| | | |
|---|---|---|
| DE | 3710489 | 11/1987 |
| DE | 4139029 | 6/1993 |
| DE | 4326037 | 2/1995 |
| DE | 9117019 | 4/1995 |
| DE | 195 37 897 | 3/1997 |

(Continued)

OTHER PUBLICATIONS

"Regulations (Standards-29 CFR) Oxygen-fuel gas welding and cutting—1910.253" by Dept, of Labor, www,osha.gov, 29 pages.*

(Continued)

*Primary Examiner*—Michael Peffley
*Assistant Examiner*—Ronald J Hupczey, Jr.

(57) ABSTRACT

A gas-enhanced electrosurgical instrument includes a hand-held applicator and a portable actuator assembly. The hand-held applicator has a gas delivery member adapted to deliver pressurized ionizable gas to the proximity of an electrode located adjacent a distal end of the applicator. The portable actuator assembly is capable of holding a source of pressurized ionizable gas, such as a cylinder or cartridge, and includes at least one controller to control the delivery of the gas from the source to the hand-held applicator and to control the delivery of electrosurgical energy to the hand-held applicator.

25 Claims, 15 Drawing Sheets

U.S. PATENT DOCUMENTS

| | | |
|---|---|---|
| 4,019,925 A | 4/1977 | Nenno et al. |
| 4,040,426 A | 8/1977 | Morrison, Jr. |
| 4,041,952 A | 8/1977 | Morrison, Jr. et al. |
| 4,043,342 A | 8/1977 | Morrison, Jr. |
| 4,057,064 A | 11/1977 | Morrison, Jr. et al. |
| 4,060,088 A | 11/1977 | Morrison, Jr. et al. |
| 4,209,018 A | 6/1980 | Meinke et al. |
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmanesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Black et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanian et al. |
| 5,700,260 A | 12/1997 | Cho et al. |
| 5,716,365 A | 2/1998 | Goicoechea et al. |
| 5,720,745 A | 2/1998 | Farin et al. |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,149,648 A | 11/2000 | Cosmescu |
| 6,197,026 B1 | 3/2001 | Farin et al. |
| 6,213,999 B1 | 4/2001 | Platt, Jr. et al. |
| 6,264,650 B1 | 7/2001 | Hovda et al. |
| 6,348,051 B1 | 2/2002 | Farin et al. |
| 6,458,125 B1 | 10/2002 | Cosmescu |
| 6,475,217 B1 | 11/2002 | Platt |
| 6,558,383 B2 | 5/2003 | Cunningham et al. |
| 6,616,660 B1 | 9/2003 | Platt |
| 6,666,865 B2 | 12/2003 | Platt |
| 6,740,081 B2 * | 5/2004 | Hilal ........................ 606/34 |
| 6,852,112 B2 | 2/2005 | Platt |
| 2001/0018587 A1 | 8/2001 | Yamamoto |
| 2002/0022838 A1 | 2/2002 | Cunningham et al. |
| 2003/0093073 A1 | 5/2003 | Platt |
| 2003/0144654 A1 | 7/2003 | Hilal |
| 2004/0088029 A1 | 5/2004 | Yamamoto |
| 2005/0015086 A1 | 1/2005 | Platt |
| 2005/0070894 A1 | 3/2005 | McClurken |

FOREIGN PATENT DOCUMENTS

| | | |
|---|---|---|
| DE | 9117299 | 4/2000 |
| DE | 19848784 | 5/2000 |
| DE | 29724247 | 8/2000 |
| EP | 0 447 121 A2 | 9/1991 |
| EP | 0 612 535 | 8/1994 |
| EP | 956827 | 11/1999 |
| EP | 1 090 599 | 4/2001 |
| EP | 1 127 551 A1 | 8/2001 |
| EP | 1 561 430 A1 | 8/2005 |
| EP | 1 570 798 A2 | 9/2005 |
| EP | 1 595 507 A2 | 11/2005 |
| FR | 1340509 | 9/1963 |
| GB | L014995 | 12/1965 |
| JP | 61-159953 | 7/1986 |
| SU | 1438745 | 11/1988 |
| WO | WO91/13593 | 9/1991 |
| WO | WO93/03678 | 3/1993 |
| WO | WO 96/24301 | 8/1996 |
| WO | WO96/27337 | 9/1996 |
| WO | WO 01/62333 | 8/2001 |
| WO | WO 02/058762 | 8/2002 |
| WO | WO 2005/016142 | 2/2005 |

OTHER PUBLICATIONS

International Search Report EP 06 01 9572 dated Nov. 21, 2006.
European Search Report.
Extended European Search Report for European Patent Application No. EP 07 00 4356 dated Jul. 2, 2007 (7 pages).
Grung et al., "Endoscopic Argon Plasma . . . Flexible Endoscopy" Surgery and Allied Technologies, No. 1, vol. 2, pp. 42-46 (Feb. 1994).

Farin et al., "Technology of Argon Plasma . . . Endoscopic Applications" Endoscopic Surgery and Allied Technologies, No. 1, vol. 2, pp. 71-77 (Feb. 1994).

Brand et al., "Electrosurgical Debulking of Ovarian Cancer: A New Technique Using the Argon Beam Coagulator" Gynecologic Oncology 39 pp. 115-118 (1990).

Hernandez et al., "A Controlled Study of the Argon Beam Coagultor for Partial Nephrectomy" The Journal of Urology, vol. 143, May (J. Urol. 143: pp. 1062-1065, 1990).

Ward et al., "A Significant New Contribution to Radical Head and Neck Surgery" Arch Otolaryngology, Head and Neck Surg., vol. 115 pp. 921-923 (Aug. 1989).

Mark H. Mellow, "The Role of Endoscopic Laser Therapy in Gastrointestinal Neoplasms" Advanced Therapeutic Endoscopy, pp. 17-21.

Silverstein et al., "Thermal Coagulation Therapy for Upper Gatrointestinal Bleeding" Advanced Therapeutic Endoscopy, pp. 79-84.

Waye et al., "Techniques in Therapeutic Endoscopy" W.B. Saunders Company, Philadelphia, PA., pp. 1.7-1.15.

International Search Report 01102843.8-2305.

International Search Report PCT/US98/19284.

European Search Report EP 05002257.3 Dated Jun. 1, 2005.

* cited by examiner

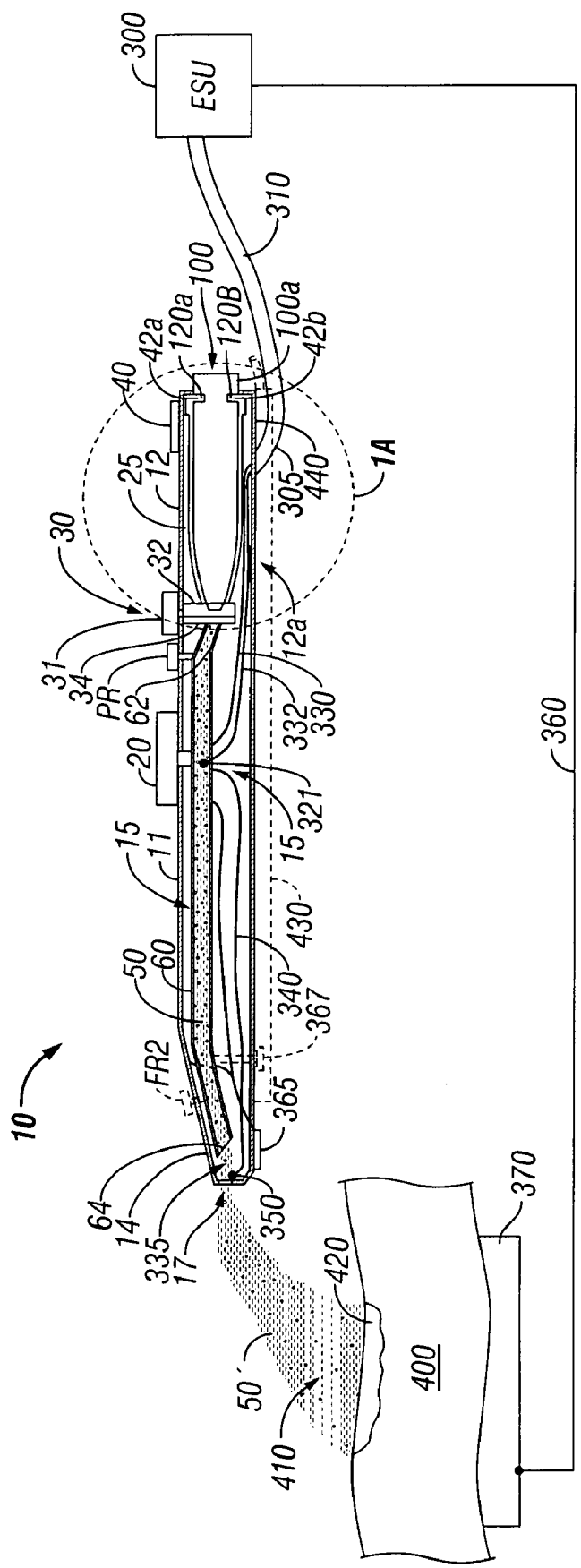
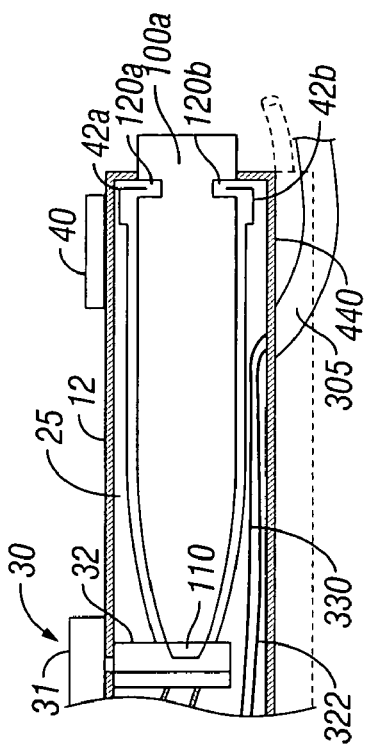
FIG. 1
FIG. 1A

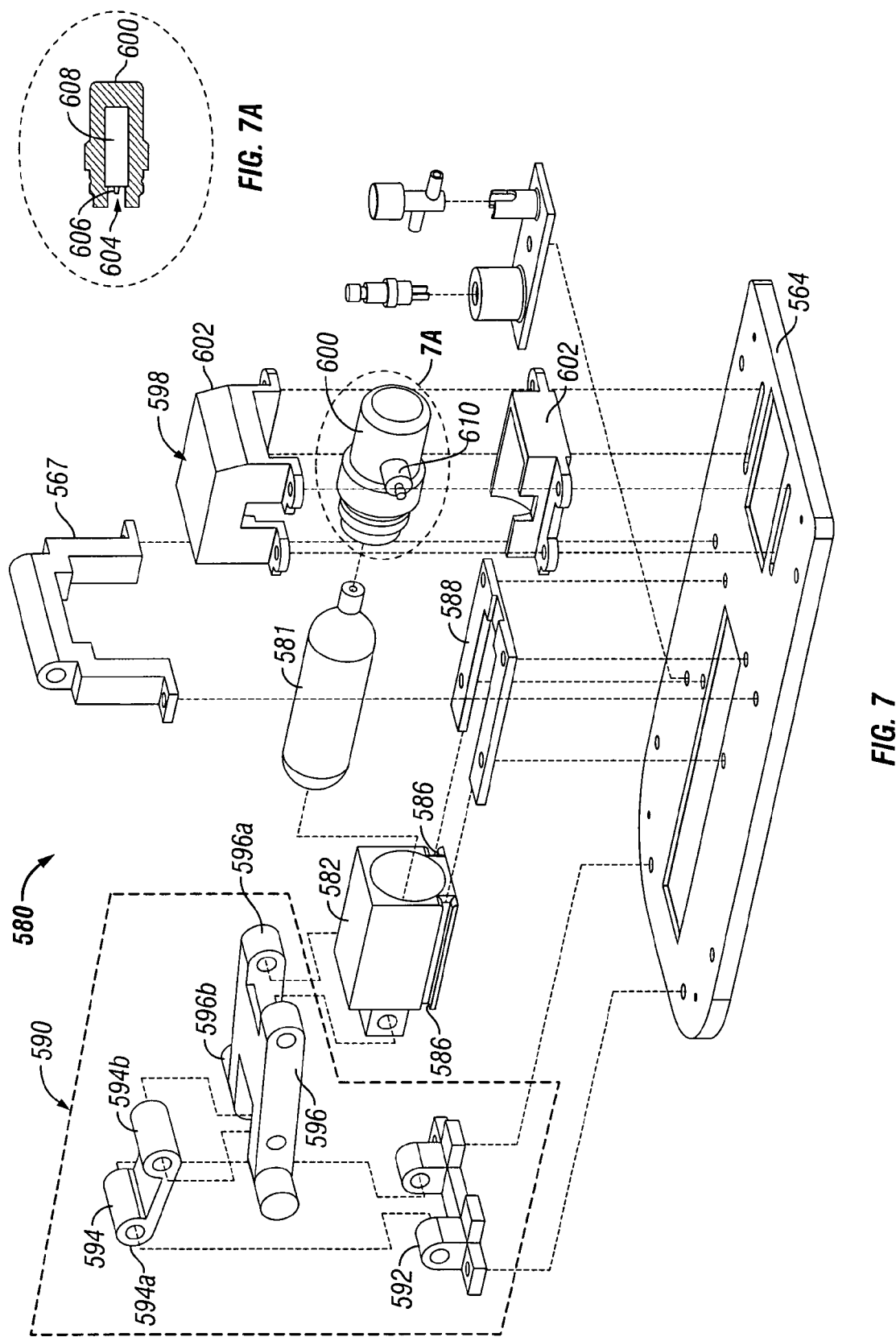

GAS-ENHANCED SURGICAL INSTRUMENT

CROSS REFERENCE TO RELATED APPLICATIONS

This application is a continuation-in-part application which claims the benefit of and priority to U.S. application Ser. No. 11/048,577 entitled "SELF CONTAINED, GAS-ENHANCED SURGICAL INSTRUMENT" filed on Feb. 1, 2005, which claims the benefit of priority to U.S. Provisional Application Ser. No. 60/541,326 entitled "SELF CONTAINED, GAS-ENHANCED SURGICAL INSTRUMENT" filed on Feb. 3, 2004, the entire contents of both applications being incorporated by reference herein.

BACKGROUND

The present disclosure relates to gas-enhanced surgical instruments with one or more portable gas supplies for use in open, laparoscopic or endoscopic procedures. More particularly, the present disclosure relates to gas-enhanced surgical instruments, including electrosurgical instruments for treating tissue, that include a selectively replaceable portable gas supply for use during medical or surgical applications.

BACKGROUND OF RELATED ART

Devices, hereafter understood to include instruments for treating tissue, for example, for tissue division, dissection, ablation, or for arresting blood loss and coagulating tissue are well known. For example, several prior art instruments employ thermic coagulation (heated probes) to arrest bleeding. However, since the probe must come into close contact with the bleeding tissue, the probe may adhere to the tissue during probe removal and may possibly cause repeat bleeding. Many surgical probes also produce an undesirable buildup of eschar on or proximate the probe tip which detrimentally affects the efficiency of the surgical instrument. Other instruments direct high frequency electric current through the tissue to stop bleeding. Again, eschar adherence may occur with these instruments. In addition, with both types of instruments, the depth of the coagulation is often difficult to control.

Other prior art devices provide a tube-like coagulation instrument in which an ionizable gas, for example argon gas, is supplied from a remote gas container or tank to the instrument and ionized by an electrode prior to the gas being emitted from the distal end of the instrument towards the bleeding tissue. The atmosphere of ionized gas is beneficial, for example, because it helps focus an arc of energy adjacent the electrode and it displaces oxygen from the area and reduces oxidative stress of the tissue. The remotely provided ionizable gas is supplied in large tanks that are typically fixed in one location in or near an operating room and not in close proximity to the patient so that a long gas supply hose is needed. Often such long hoses add to the clutter in the operating room and are distracting to the operating room staff.

Unlike the prior art instruments, the instruments and small gas containers of the present disclosure are easy to handle and manipulate. These instruments may be configured to include one or more of a variety of features, e.g., flow and/or pressure regulators, pressure relief valves, gauges, indicators, sensors and control systems that can be tailored to fit the surgical procedure. The instruments and the controls associated therewith may be controlled by hand and/or foot by the user which accordingly, provide the opportunity for obtaining optimized results. The small gas containers and their contents can also be tailored (e.g., in terms of use of a particular inert gas or gas mixture, gas pressure, volume, flow rate, etc.) to fit the particular instrument and/or procedure also providing the opportunity to obtain optimized results.

SUMMARY

The present disclosure relates to gas-enhanced electrosurgical instruments for providing ionized gas to a surgical site. In one embodiment, the electrosurgical instrument includes a hand-held applicator and an actuator assembly. Preferably, the hand-held applicator has a gas delivery member, e.g., a tube, used to deliver pressurized ionizable gas to the proximity of an electrode located adjacent a distal end of the applicator. The portable actuator assembly is configured to hold a sealed portable source of pressurized ionizable gas, such as a cylinder or cartridge, and includes at least one controller that controls the delivery of the gas from the source and electrosurgical energy to the hand-held applicator. In operation, actuation of the at least one controller causes gas from the source to be delivered to the proximity of the electrode through the gas delivery member and causes electrosurgical energy to be delivered to the electrode creating ionized gas that is emitted from the hand-held applicator toward the surgical site.

In one embodiment, the hand-held applicator includes a tubular frame having a port for emitting the ionized gas at its distal end and the tube extends through the tubular frame. In this embodiment, the electrode is located between the port and the end of the tube so that the gas is ionized just prior to being emitted from the tubular frame. The portable actuator assembly may include a housing having a pivotably secured actuator, e.g., a foot pedal, a gas source module within the housing configured to hold the source of pressurized ionizable gas, and a first controller located within the housing and coupled to the gas source module. The housing actuator is used to actuate the first controller, e.g., a valve, to cause the delivery of gas from the source of pressurized ionizable gas to the hand-held applicator. The housing actuator can also be used to actuate a second controller, e.g., a switch, located in the housing and used to deliver electrosurgical energy to the hand-held applicator. Preferably, the housing actuator actuates the first controller prior to actuating the second controller.

The source of pressurized ionizable gas may be a cylinder, canister, cartridge or other suitable container capable of holding pressurized gas, and the gas may be argon or other inert gas capable of being ionized for surgical procedures or a mixture of such inert gases.

Preferably, the gas source module in the housing includes a movable receptacle that holds the source of pressurized ionizable gas. Movement of the receptacle facilitates movement of the source between engaged and disengaged positions. A locking assembly is provided to lock the receptacle in place when the source of pressurized ionizable gas is in the engaged position, and a coupler assembly engages at least a portion (e.g., an outlet) of the source to form a hermetic seal around the outlet so that gas does not escape into the housing. Typically, the source has a sealed outlet, and the coupler assembly is configured to rupture the sealed outlet when the source is moved to the engaged position.

The electrosurgical instrument disclosed herein can be used for different applications in different types of surgical procedures. For example, electrosurgical instrument could be configured to coagulate body tissue, and the instrument could be configured and adapted for use in an open, laparoscopic or endoscopic surgical procedures.

BRIEF DESCRIPTION OF THE DRAWINGS

FIG. 1 is a side schematic view of an electrosurgical coagulator according to the present disclosure;

FIG. 1A is an enlarged view of the encircled portion of FIG. 1;

FIG. 7 is a perspective view with parts separated of one embodiment of a gas source module in the actuator assembly;

FIG. 7A is a side cross-sectional view of one embodiment of a gas supply coupler assembly according to the present disclosure;

DETAILED DESCRIPTION

Figure 4:
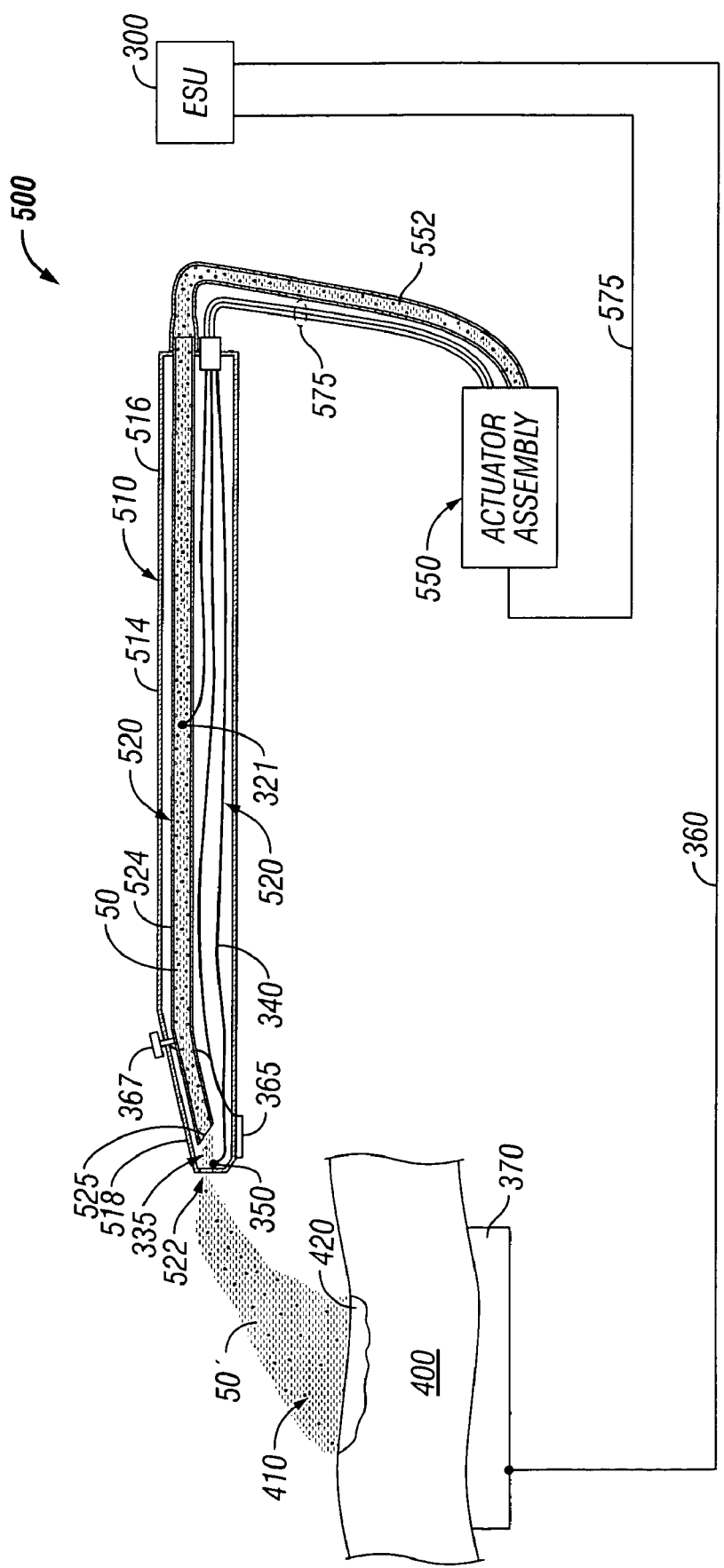
FIG. 4 is a side schematic view of an alternative embodiment of the electrosurgical instrument according to the present disclosure, showing an applicator and an actuator assembly.
Figure 19:
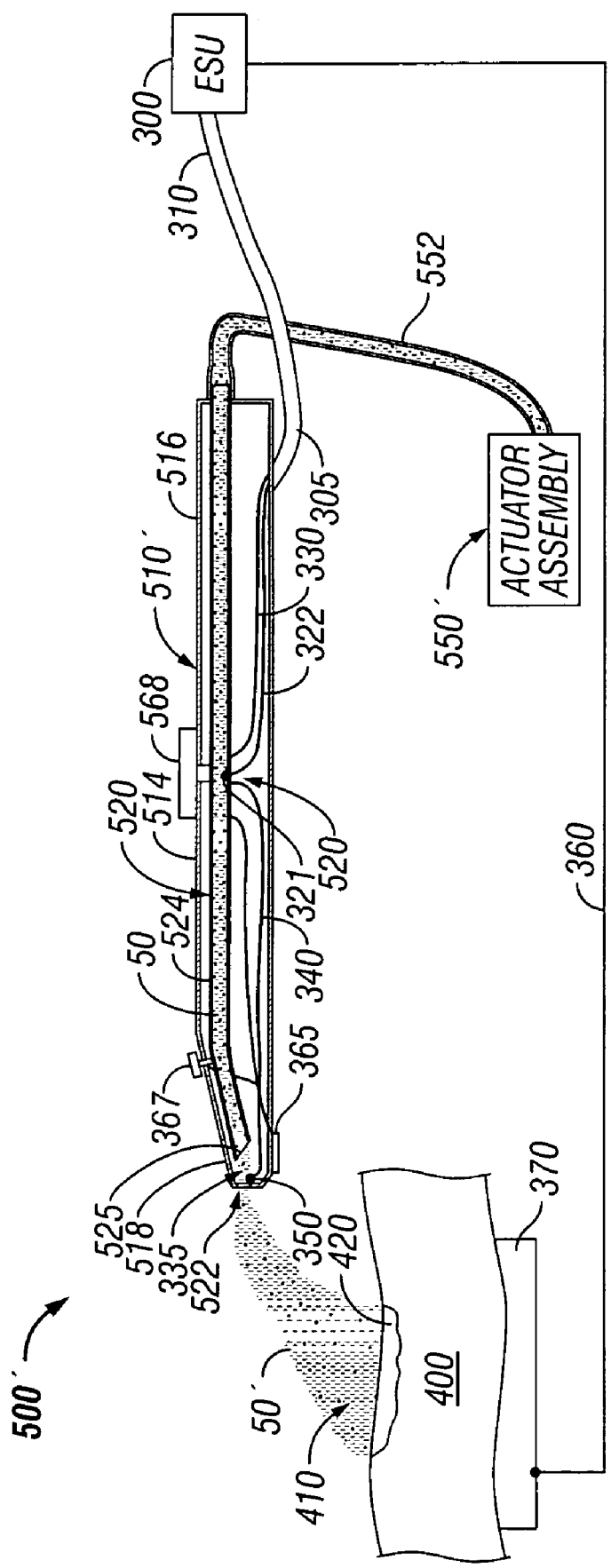
FIG. 19 is a side schematic view of an alternative embodiment of the electrosurgical instrument according to the present disclosure, showing a hand-held applicator with an actuator and the actuator assembly.
Figure 20:
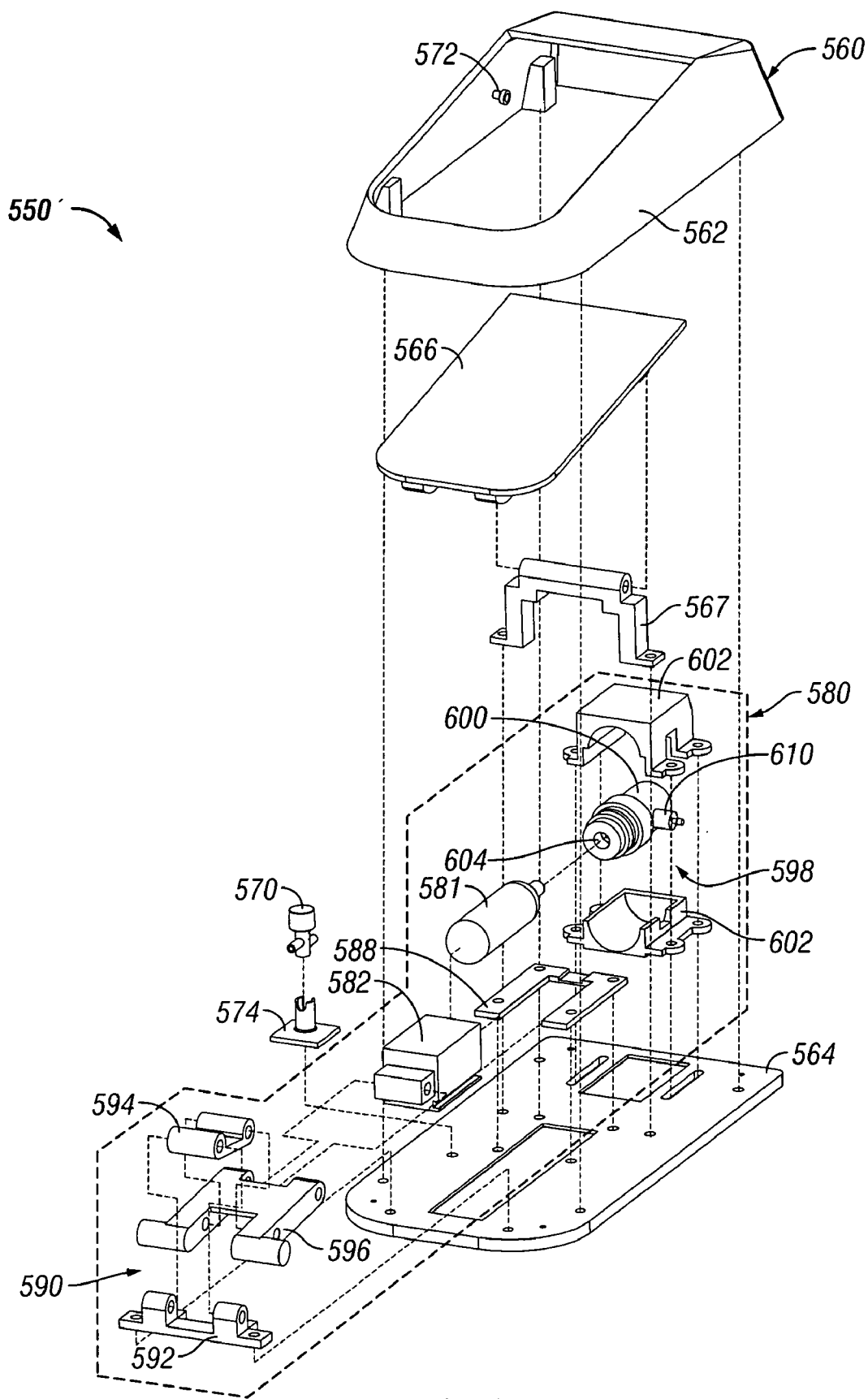
FIG. 20 is a perspective view with parts separated of the actuator assembly of FIG. 19.

This application discloses embodiments of electrosurgical apparatus or instruments that are adapted for use with or include a portable supply of pressurized inert gas for providing ionizable gas to a surgical or operative site. FIG. 1 shows one embodiment of a gas-enhanced electrosurgical instrument generally designated 10 having a self-contained supply of pressurized ionizable gas. FIGS. 4 and 19 show different embodiments of gas-enhanced electrosurgical instruments generally designated 500 and 500' having portable sources of pressurized ionizable gas remote from the hand-held applicator. The electrosurgical instruments of the present disclosure may be used for various surgical functions, such as arresting bleeding tissue, desiccating surface tissue, eradicating cysts, forming eschars on tumors, or thermically marking tissue. For ease of description, the instrument described herein is configured for use as a coagulator to arrest bleeding tissue. However, those skilled in the art will appreciate that certain modifications can be made to the electrosurgical instruments of the present disclosure so that the instruments can perform other surgical functions without departing from the scope of this disclosure. Moreover, while it is preferable to use argon as the ionizable gas for promulgating coagulation of tissue, for other surgical functions another ionizable gas or a combination of ionizable gases may be utilized to achieve the desired result.

Referring to FIG. 1, coagulator 10 is dimensioned to be pencil-like or hand-held, including robotically, for use during open surgical procedures, however, it is envisioned that a similar instrument or coagulator may be configured, for example, with a pistol grip or handle dimensioned for laparoscopic or endoscopic surgical procedures. Further, although the basic operating features of an open electrosurgical coagulator 10 are described herein, the same or similar operating features may be employed on or used in connection with a laparoscopic or endoscopic electrosurgical coagulator or instrument, manually or robotically operated, without departing from the scope of the present disclosure. The term "electrosurgical energy" herein refers to any type of electrical energy which may be utilized for medical procedures.

As shown in FIG. 1, coagulator 10 includes a frame, shown as an elongated housing 11, having a proximal end 12, a distal end 14 and an elongated cavity 15 extending therethrough, for supporting and/or housing a plurality of internal and/or external mechanical and electromechanical components thereon and therein. In this disclosure, as is traditional, the term "proximal" will refer to the end of coagulator 10 (or other element) which is closer to the user, while the term "distal" will refer to the end which is further from the user.

Distal end 14 of housing 11 includes a distal port 17 which is designed to emit, expel or disperse gas emanating from an elongated gas supply channel or tube 60 that in this embodiment runs generally longitudinally through frame or housing 11 of coagulator 10. Tube 60 is for supplying pressurized gas 50 to the proximity of an active electrode 350 located adjacent distal end 14 of housing 11. Electrode 350 is proximal of port 17 such that the gas that is emitted from port 17 is ionized. Elongated housing 11 includes a receptacle 25, typically positioned adjacent its proximal end 12, which receptacle can be or be part of a unitary or integral handle portion 12a of housing 11. Receptacle 25 is dimensioned to securely engage and receive or seat a gas pressurized container, canister, cartridge or cylinder 100 therein. Cylinder 100 contains a surgical gas, e.g., a noble or inert gas, or mixture of noble or inert gases. References herein to inert gas or gases are understood to include noble gas or gases. The preferred inert gas is argon. Cylinder 100 is relatively small, single use and disposable. The cylinder is of standardized design and certified for transportation requirements. Moreover, cylinder 100 is designed and/or sized to be incompatible with other commercial products such as whip cream dispensers and the like which use nitrogen and CO2 cartridges for other purposes. Details of gas cylinder 100 and its selective engagement with or connection to housing 11 are discussed in more detail below with respect to FIGS. 2A-2C.

Elongated gas supply tube 60 is adapted and dimensioned to channel or carry pressurized gas 50 from cylinder 100 through a regulator or valve 30 to or through distal end 14 of coagulator 10 for ionization, typically prior to the gas emitting and dispersing from distal port 17. Regulator or valve 30 can be part of or attached to cylinder 100, housing 11, or actuator 31. It is envisioned that distal port 17 or distal end 14 may be configured to facilitate or promote the dispersion of the ionized gas plasma 50' from distal port 17 in a uniform and consistent manner. For example, distal end 14 may be tapered on one, both or all sides thereof to direct the ionized plasma 50' toward surgical or operative site 410. Alternatively, distal port 17 may be configured to disrupt or aggravate the dispersion or flow of gas plasma 50' exiting distal port 17 to enhance coagulation by creating a more turbulent gas flow. It is contemplated that many suitable devices, e.g., screws, fans, blades, helical patterns, etc., may be employed to cause gas plasma 50' to flow more or less turbulently or with other predetermined flow characteristics through tube 60 and/or out of distal port 17.

Elongated housing 11 is connected, for example, by an electrical cable 310, to a source of electrosurgical energy generally designated ESU, e.g., an electrosurgical generator 300. As mentioned above, proximal end 12 includes a receptacle 25 which receives, securely engages and seats cylinder 100 therein. Receptacle 25 and/or cylinder 100 need not be, as in the case of a single use disposable instrument, but may be configured to allow cylinder 100 to be selectively removable and replaceable within receptacle 25. For example and as best shown in FIG. 1, proximal end 12 of elongated housing 11, or receptacle 25 may include a locking mechanism 40 which upon insertion of a cylinder 100 into receptacle 25 automatically (or manually) releasably locks the cylinder 100 securely within receptacle 25. By unlocking locking mechanism 40, cylinder 100 may be removed and replaced with another cylinder 100.

It is envisioned that the locking mechanism 40 may be any suitable device or arrangement, e.g., a collar or clamp which provides adequate lever advantage to set the cylinder 100 against its end seal. The collar or clamp may be designed to allow the cylinder to be disengaged from the seal but retained within the receptacle 25 until the remaining pressurized gas is vented or otherwise relieved. For example, the locking mechanism 40 may include two or more opposing spring clamps 42a, 42b which mechanically engage a corresponding one or more notches or cut outs 120a, 120b formed in the outer surface of gas cylinder 100. As can be appreciated, upon insertion of cylinder 100 into receptacle 35, the spring clamps 42a, 42b are positioned to allow entry of cylinder 100 into receptacle 25 until the spring clamps engage the notches 120a, 120b. It is envisioned that a locking mechanism 40 with spring clamps can be configured and adapted for releasably locking and quickly releasing the locking of cylinder 100 in receptacle 25.

The relative positioning and mechanical engagement of spring clamps 42a, 42b in notches 120a, 120b fully seats cylinder 100 within the receptacle such that a distal end 110 of cylinder 100 fully engages valve 30. The full seating of cylinder 100 in receptacle 25 can affect piecing or puncturing of the sealed distal end 110 of gas cylinder 100. Upon opening or actuation of valve 30, gas 50 is dispersed to elongated supply tube 60 as explained below.

Figure 2A:
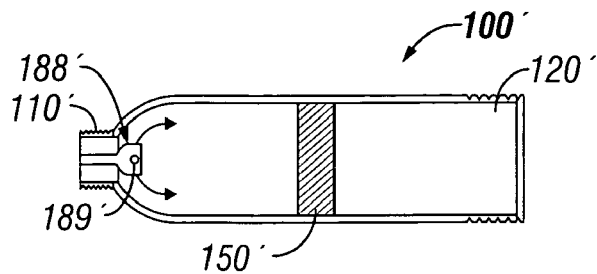
FIG. 2A is an enlarged, schematic sectional view of an alternate embodiment of a gas cartridge for use with the electrosurgical coagulator of FIG. 1 having a color coded identification band and a safety valve.

A variety of other locking mechanisms may be utilized to secure gas cylinder 100 to or within receptacle 25. For example, the distal end 110 of cylinder 100 of FIG. 1a may be configured, e.g., threaded (as shown as 110' in FIG. 2A) to threadedly engage valve 30. Alternatively, as also shown in FIG. 2A, the proximal end of cylinder 100' may include threads 120' which threadably engage the interior of receptacle 25 (not shown). In this instance it may be advantageous to include or provide a rubber O-ring or washer in the proximity of the threads to protect against undesirable gas leakage.

Alternatively, proximal end 12 of housing 11 may be adapted to have an externally threaded collar or sleeve that extends axially outwardly and have an internally threaded screw closure cap. With a cylinder seated in receptacle 25, the screw closing of the cap would push cylinder 100 distally against the bias of a spring onto an axially disposed piercing member to thereby break the seal at the distal tip of the cylinder. Removal of the closure cap would permit removal and replacement of the cylinder. The cap can be adapted to safely vent pressurized gas from the interior of the receptacle 25 should the seal on the distal end of the cylinder be lost or damages thus preventing the receptacle from bursting in the event of an internal overpressure. Additionally, the cap may be configured to include a pressure regulator or valve to control flow through seal opening. As can be appreciated, this safety feature may be designed to limit the flow from the cylinder and protect the user if the cylinder becomes damaged during handling. Other locking mechanisms are also envisioned, for example an over-the-center lever arrangement for pulling a yoke around the end of cylinder 100, snap locks, spring locks on the cylinder 100, locking levers, bayonet style locks, and locking dials or tabs, etc.

The cylinder 100 may also include various ergonomically friendly features such as rubber gripping elements or contoured walls to facilitate insertion into the housing 11 and handling especially during wet operative conditions. Additionally and as described in more detail below, the cylinder may be color coded to specify any or a combination of the following: cylinder contents (gas type and amount); initial pressure reading prior to activation; a specific flow rate; or specify use for a given procedure.

Electrosurgical instrument 10 includes at least one actuator, e.g., a dial or button, generally designated 31, for actuating and selectively adjusting the flow of pressurized inert gas 50 from cylinder 100 to the proximity of active electrode 350, and for actuating and selectively adjusting the delivery of electrosurgical energy from the source, i.e., from generator 300, to the active electrode 350 for ionizing the inert gas for use at the surgical site 410. Actuator 31 can also operate as the actuator for actuating delivery of electrosurgical energy from the source. Actuator 31 may be referred to herein as the first actuator. It is envisioned that instead of being located in housing 11, one or more of the actuators, regulators and/or valves described herein may be located in a foot switch appropriately connected to coagulator 10.

Electrosurgical instrument or coagulator 10 can also include a second actuator, here shown as a button-like trigger 20, for actuating the delivery of electrosurgical energy from the source, e.g., from generator 300, through cable 310 and leads 322, 330 to the active electrode 350 for ionizing the inert gas for use at the surgical site 410. Trigger 20 can be attached to or mounted, for example, on or atop or through elongated housing 11. Trigger 20 may be any type of known trigger, e.g., a rocker switch, a handswitch, a footswitch, a slide switch, a dial, a button, a lever, etc., which, upon actuation thereof, electrically communicates with electrosurgical generator 300 to allow the selective delivery of electrosurgical energy to active electrode 350.

Active electrode 350 can be attached to or mechanically engaged with the distal end of the housing and positioned adjacent to or at an operating site 410. Active electrode 350 is positioned adjacent the distal end of frame or housing 11 between the distal end of tube 60 and distal port 17, although the active electrode can be located just to the exterior of port 17. For example, active electrode 350 can be mounted to an elongated member that is supported within housing 11 and that extends outside of the housing, such that the electrode is positioned just outside of the port. Active electrode 350 need not be as shown. It can be a conductive elongated member in the form of a blade, needle, snare or ball electrode that extends from an electrosurgical instrument and that is suitable, for example, for fulguration, i.e., coagulation, cutting or sealing tissue.

As shown and in most monopolar electrosurgical systems, a return electrode or pad 370 is typically positioned under the patient and connected to a different electrical potential on electrosurgical generator 300 via cable 360. During activation, return pad 370 acts as an electrical return for the electrosurgical energy emanating from electrosurgical coagulator 10. It is envisioned that various types of electrosurgical generators 300 may be employed for this purpose, such as those generators sold by Valleylab, Inc.—a division of Tyco Healthcare Group LP, of Boulder, Colo.

It is envisioned that trigger 20, upon actuation thereof, is designed to energize electrode 350 in a simple "on/off" manner, e.g., when the trigger is depressed (or otherwise moved or manipulated, e.g., twisted (dial switch), rocked (rocker switch), or slid (slide switch)). Alternatively, it is contemplated that the electrical intensity from generator 300 may be selectively regulated by trigger 20, such that the user can alter the electrosurgical effect at operative site 410. For example a pressure sensitive trigger or regulator may be utilized to control the amount of electrosurgical energy that is conducted to electrode 350 which, as described below with respect to the operation of coagulator 10, effects coagulation of tissue 400. Triggers and actuators that are contemplated include those such as described in commonly-owned U.S. Provisional Application Ser. No. 60/424,352 and commonly-owned U.S. application Ser. No. 10/251,606, the entire contents of each of which are incorporated by reference herein, without intention of being limited to the same.

U.S. application Ser. No. 10/251,606, now publication No. 04-0092927 discloses an electrosurgical instrument having variable controls, a housing, and an electrocautery blade or electrode extending from the housing and connected to a source of electrosurgical energy. An actuator button supported on the housing is movable, e.g., depressed, or rocked or slid, from a first position to at least a subsequent position, preferably to a series of discrete subsequent positions wherein each subsequent position corresponds to a specific amount of energy being transmitted to the blade. A transducer, e.g., a pressure transducer, or other suitable circuit element, is electrically connected between the activation button and the source of electrosurgical energy. The transducer is configured to transmit an electrical output signal (or a range of output signals) to the energy source correlating to the selected movement or position(s) of the activation button. The source correspondingly supplies an amount or range of electrosurgical energy emission to the blade dependent upon the electrical output signal(s).

The above actuator and selectively adjustable system can be employed using at least one actuator, actuator 31, for actuating and selectively adjusting the flow of pressurized gas from cylinder 100, e.g., via regulator and valve 30, and for actuating and selectively adjusting delivery of energy from the source. Such can be achieved by employing, for example, a suitable transistor that produces a signal or two signals or different sets of output signals based on movement of the actuator button. The signal (or one signal or set of signals) is sent to and is suitable for actuating actuator 31 or regulator and valve 30 to actuate movement-correlated corresponding selectively adjusted flow of gas from the cylinder. The signal (or the other signal or set) is sent to and is suitable for actuating trigger 20 to deliver energy from the source. A similar suitable actuator system can be employed with one transistor to actuate a first actuator, actuator 31, for actuating and selectively adjusting the flow from cylinder 100, and a second transistor to actuate a second actuator, trigger 20, for actuating and selectively adjusting delivery of energy from the source. It is envisioned that instead of being located in housing 11, trigger 20 can be located in a foot switch appropriately connected to electrosurgical generator 300 and coagulator 10.

It is contemplated that the at least one actuator, e.g., actuator 31, is adapted or operated to actuate the release of pressurized gas 50 prior to actuating the delivery of electrosurgical energy from generator 300. When there is a first actuator and a second actuator, it is contemplated that the instrument or coagulator includes one or more elements, e.g., circuitry, or mechanical or electromechanical mechanism(s), for timing the flow of gas from cylinder 100 and the delivery of energy to the electrode. In one particularly useful embodiment, the first actuator is activated prior to the activation of the second actuator.

It is also contemplated that trigger 20 (or generator 300) may cooperate with one or more sensors 365 which can be attached to instrument 10, housing 11 or electrode 350 and which, for example, continually measures or monitors a condition at operative site 410, e.g., the amount of tissue coagulation, and relays the information back to generator 300 or trigger 20. For example, a control system or a safety circuit (not shown) may be employed which automatically (e.g., through a shut-off switch) reduces pressure or partially closes valve 30 if an obstruction is indicated. Alternatively or in addition, the safety circuit may be configured to cut off the energy to tissue 400 and/or activate or release a pressure relief valve (e.g., a safety release valve generally designated 367) to release the pressure of the pressurized gas based upon a sensed condition (e.g., an embolic condition or concern) by a sensor 365 or by the surgeon. It is also envisioned that based upon the sensed condition, gas cylinder 100, e.g., by valve 30, can be partially modulated, inactivated, ejected (or released) from engagement with valve coupling 32, or valve 30 may be automatically fully de-activated or closed. Alternatively, sensor 365 may provide feedback to trigger 20 or generator 300 to optimize coagulation of the tissue 400 based upon distance from the tissue deduced from the measured back pressure in supply tube 60, based upon tissue type or based upon tissue response. A second sensor 321 may be employed to measure the flow of gas 50 through gas supply tube 60, and may be electrically connected to a flow regulator, e.g., valve 30, to automatically regulate the flow of gas from cylinder 100 to electrode 350.

As best shown in FIG. 1, actuator 31 includes regulator and valve 30 which is mounted to and through elongated housing 11 and which can be dimensioned to mechanically engage (and preferably also puncture or otherwise engage and open) the sealed outlet at distal end 110 of selectively removable gas cylinder 100. Gas cylinder 100 can be removable in a reusable or disposable version of the instrument. In one particularly useful embodiment, the mechanical engagement and securement of gas cylinder 100 and valve 30 involves a quick-release type mechanism or other simple attachment mechanism which can be employed on and/or or as part of cylinder 100, receptacle 25 and/or housing 11 to enable the user to quickly and accurately engage and disengage and remove and replace gas cylinder 100. For example, various springs, levers, latches, slides and frictional engagement members, (not shown) may be employed to facilitate loading and quick removal of cylinder 100. As mentioned above, locking mechanism 40 may be employed to permanently or releasably secure cylinder 100 within receptacle 25.

Actuation of actuator 31 activates regulator and valve 30. Regulator and valve 30 selectively controls or regulates the flow of gas from cylinder 100 to electrode 350. Regulator and valve 30 may include a cylinder interface or coupling 32 and a plenum 34. Actuator 31 or regulator and valve 30 selectively adjusts plenum 34 to selectively regulate the amount or flow of gas 50 from gas cylinder 100, to supply tube 60 and to electrode 350.

It is envisioned that actuator 31 may be incrementally adjustable (i.e., rotatable, slideable or pressure sensitive) to provide tactile feedback to the user relating to the flow of gas 50. As can be appreciated, plenum 34 is disposed between the regulator portion of the regulator and valve 30 and the proximal end 62 of supply tube 60. As mentioned above, coupling 32 mechanically engages (e.g., threadably engages, snap fits, friction-fits, slide fits, spring mounts, bayonets, or otherwise) cylinder 100, seals the juncture with cylinder 100, and also breaks, pierces or otherwise opens the sealed distal end or outlet of cylinder 100 upon insertion of the cylinder 100 into receptacle 25. Although it is preferred that actuator 31 include regulator and valve 30, regulator and valve 30 can include actuator 31. Regulator and valve 30 may be referred to herein as a first flow regulator for selectively regulating the flow of pressurized gas from cylinder 100.

In one embodiment, coagulator 10 can include separate pressure regulators, valves and/or flow regulators which are separated and spaced down the length of the coagulator 10. For example, a second flow regulator, e.g., "FR2" may be included which selectively regulates the flow of pressurized gas to electrode 350. In yet another embodiment, coagulator 10 can include a pressure regulator, e.g., "PR", for regulating the pressure of the pressurized gas that flows to electrode 350. Valve 30 may include a pressure regulator having a pressure relief valve in communication with cylinder 100 for regulating and/or relieving the pressure of the pressurized gas in the cylinder. Coagulator 10 also may include a flow limiter. For example, valve 30 may include a flow limiter for limiting the flow of pressurized gas to electrode 350 to a selected level. In one particularly useful embodiment, a pressure relief valve or "burp valve" may be included which is disposed proximal to the flow limiter or plenum to permit gas to escape from the channel 60 thereby preventing a build-up of pressure at opening 17 as a result of partial of full occlusion of opening 17. A flue 430 (see FIG. 1) may be included which transfers the relieved gas flow to the proximal end of the coagulator 10.

Distal end 110 of cylinder 100 is hermetically sealed when and after it is mounted to and mechanically engaged with coupling 32 to avoid undesirable gas leakage from the mechanical connection. The end seal may be formed through metal-to-metal contact, by an elastomeric land at the face 110 of cylinder 100 or an elastomeric ring encircling cylinder 100. As can be appreciated, various rubber seals, gaskets, flanges or the like (not shown) may be employed to accomplish this purpose.

It is envisioned that valve 30 be opened, e.g., manually, to a desired flow rate prior to activation of electrode 350 to ionize the plasma to coagulate tissue 400. The same button, actuator or lever that actuates the delivery of energy would also activate regulator and valve 30 and the flow of gas. For example, the movement of a lever would actuate regulator and valve 30 and the flow of gas prior to continued movement of the lever to actuate delivery of energy from the generator 300. It is also contemplated that actuator 31 or valve 30 may be automatically regulated to communicate with trigger 20 and be automatically controlled by activation of trigger 20. For example, the user may select a flow rate by actuating actuator 31 (which may include a visual indicator or the like to allow the user to readily determine flow rate) such that upon actuation of trigger 20, regulator and valve 30 initiates the flow of gas 50 through tube 60 to the an ignition point 355 proximate electrode 350. Electrode 350 can, in turn, be activated to ionize the gas 50 and force the ionized gas plasma 50' at the tissue or operating site 410. Alternatively, actuation of actuator 31 or regulator and valve 30 can automatically activate actuation of trigger 20 and flow of electrosurgical energy to electrode 350.

After actuation of trigger 20 and initiation of gas flow to ignition point 335, the ignition of the electrode 350 is delayed either mechanically, electro-mechanically or utilizing delay circuitry or a delay algorithm to preferably enhance delivery of plasma 50' to operating site 410. As can be appreciated, the delay circuitry or algorithm may be incorporated in trigger 20, valve 30 or generator 300.

During use, ionizable gas 50 is supplied under pressure from gas cylinder 100 to regulator and valve 30 (or simply a flow regulator) and, upon selective actuation of actuator 31, the gas flows to ignition point 335 near electrode 350 where gas 50 is ionized into a gas plasma 50' before being distributed, dispersed or dispensed out of distal end 17 to operating site 410. During use, the user may selectively alter the gas flow rate and/or the intensity of the energy emanating from electrode 350 to meet a desired surgical effect.

Gas cylinder 100 is relatively small and contains an appropriate or sufficient amount gas 50 for a given surgery of short duration. Cylinder 100 is typically for single use, and is disposable. It may be replaced as needed during the surgical procedure if it requires a longer or different gas application than provided by a single gas cylinder. As can be appreciated, different gas cylinders 100 may be utilized for different surgeries which have different gas requirements, e.g., in terms of types, amounts, pressures and/or flow rates. The gas pressure of cylinders 100 is typically about 3000 psi or less. Gas cylinders 100 have a volume of about 100 cc's or less.

Cylinders 100 containing about 4 liters of gas and a flow time of about 2 minutes have been found suitable for a typical coagulation procedure. For such procedures, the flow rate provided by the cylinder can range from about 0.2 liters/min. to about 4 liters/min, and the nominal flow rate may be about 2 liters/min. It is envisioned that cartridge 100 may be pre-configured to deliver gas at a predefined flow rate, and coagulator 10 may be configured without a flow regulator or flow valve 30 in or on elongated housing 11. Instead, elongated housing 11 may simply include an "open" and "close" switch (not shown) which blocks or releases the flow of gas from the gas cylinder 100 depending upon the position of the switch. As a result thereof, when opened, coagulator 10 relies on the predetermined flow rate of the gas 50 exiting the gas cylinder 100 under pressure.

The gas flow rate employed is dependent upon factors such as the instrument being used and/or the type of surgery or procedure to be performed. Different gas cartridges, e.g., cylinder 100', can be pre-marked or coded, e.g., visibly, with a color, e.g., a colored band 150' (see FIG. 2A) to indicate a specific gas, as-filled flow rate or suitability for a particular instrument, procedure or application. Thus, a user may pick the appropriate color which specifically relates to a desired specific gas, flow rate and intended surgical use. Since cylinders 100 are easily replaceable, during surgery the user may opt to replace a cylinder 100 with a different cylinder 100' with a different flow rate (different color band 150'). Cylinder 100 may include a knob, e.g., 100a at the proximal end of the cylinder to facilitate manipulation of the cylinder.

FIG. 2A shows an embodiment of a gas cylinder 100' which includes a safety release pressure stop valve 188' which is designed to automatically prevent flow of gas from, cylinder 100' when the cylinder is removed. More particularly, upon release of the cylinder 100' from coupling 32, a ball 189' (in a ball check valve) or some other movable obstruction automatically moves distally to block the passage of gas 50 through distal end 110' of the cylinder 100'. Upon insertion or engagement of the cylinder 100' into coupling 32, a pin or other protruding element (not shown) forces ball 189' proximally to allow the release of gas 50 from cylinder 100'. As can be appreciated, many different types of release pressure stops may be employed to accomplish the same or similar purpose and the above-described release pressure stop valve 188' is only one example. It is contemplated that cylinder 100 or the like, e.g., 100''', can include a safety pressure release valve "SPRV" to vent the gas prior to or when an active cylinder 100 is removed from receptacle 25 and/or to safely control release of cylinder internal gas overpressure. It is also contemplated that coagulator 10, e.g., receptacle 25, can include a pressure relief valve 440 in communication with cylinder 100 for relieving the pressure of the pressurized gas in the cylinder.

Figure 2B:
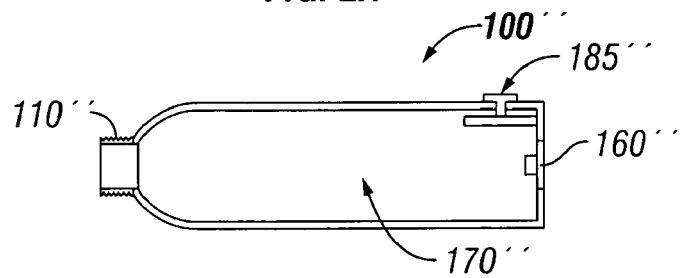
FIG. 2B is an enlarged, schematic sectional view of a gas cartridge for use with the electrosurgical coagulator of FIG. 1 having a volume gauge and a refilling port.

As best shown in FIG. 2B, an embodiment of gas cylinder 100" may include a gauge 185" which measures and indicates the amount of pressurized gas left in cylinder 100" at any given time. A visual or audible indicator or sensor (not shown) may be employed to alert the user of a low gas condition. Gas cylinder 100" may also include a fill port or refill valve 160" which enables the user to selectively refill interior 170" of gas cylinder 100" without removing the cylinder from within receptacle 25 of instrument 10.

Figure 2C:
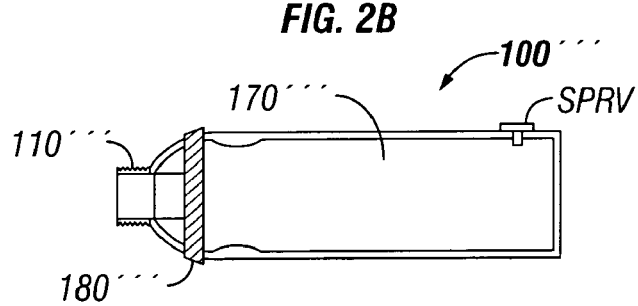
FIG. 2C is an enlarged, schematic sectional view of a gas cartridge for use with the electrosurgical coagulator of FIG. 1 having a flow regulator.

FIG. 2C shows another embodiment of gas cylinder 100''' which includes a valve 180''' disposed thereon which allows a user to selectively regulate gas flow from interior chamber 170''' through distal end 110''' and to coagulator 10. As such, a valve would not necessarily be needed within coagulator 10 and the user can selectively regulate gas 50 by rotating (or otherwise adjusting) valve 180''' as needed.

Figure 3A:
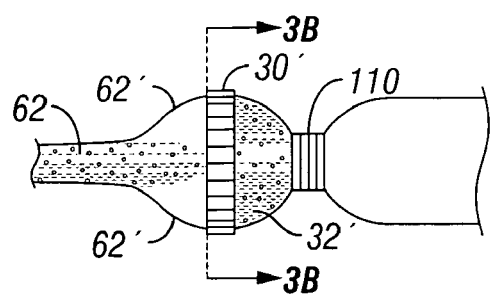
FIG. 3A is a greatly-enlarged, schematic side view of an iris-like flow regulator for use with the electrosurgical coagulator of FIG. 1.
Figure 3B:
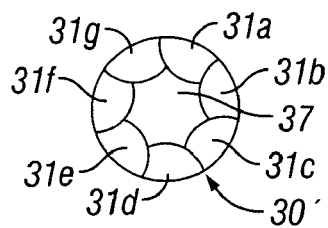
FIG. 3B is a cross sectional view of the iris-like flow regulator taken along line 3B-3B of FIG. 3A.

FIGS. 3A and 3B show an embodiment of a flow control valve, here shown as a rotary iris-like valve 30', which may be utilized within coagulator 10 (or with the gas cylinder 100''' as mentioned above) for selectively controlling the flow of pressurized gas from the cylinder. Iris valve 30' may be disposed between a coupling 32' and a flared portion 62' of proximal end 62 of supply tube 60. Upon rotation of iris valve 30' in a first direction, a series of interleaved portions 31a-31g move to radially reduce or condense the dimensions of passageway or opening 37 to limit gas flow therethrough and to the flared portion 62' of gas supply tube 60. Upon rotation of iris valve 30' in the opposite direction, the interleaved portions 31a-31g move to radially expand the dimensions of opening 37, enhancing gas flow therethrough and to the flared portion 62' of the supply tube 60.

It is envisioned that a corona return electrode or corona start electrode (not shown, but known in the art) may be utilized with electrode 350 to initiate a plasma arc. The corona return electrode may be placed on or within housing 11 located near distal end 14 or distal port 14. The corona return electrode is electrically connected to return path 360 of electrosurgical generator 300. The function of the corona return electrode is to establish a non-uniform electrical field with active electrode 350. The non-uniform electric field will cause the formation of a corona near active electrode 350, which will thereby aid in the ignition of gas 50 as it flows out of distal port 17 of the housing 11. A dielectric member (not shown) may be positioned to separate active electrode 350 from the corona return electrode.

It is also envisioned that the coagulator 10 may be configured to include a two-stage regulator (not shown) instead of a burp valve. In particular, this may be particularly advantageous for use with a laparoscopic device wherein the gas flow may be affected by insufflation pressure in the operating cavity.

Moreover, although shown as a pencil-like electrosurgical instrument in the drawings, it is envisioned that the electrosurgical instrument may include a pistol grip-like handle which enables the user to handle the instrument like a pistol. It is also contemplated that the cylinder may be dimensioned for selective engagement (i.e., insertion) within and disengagement (i.e., release) from the handle. Alternatively, the handle may be selectively pivotable for handling the electrosurgical instrument in different orientations, e.g., from an offset position relative to the housing for handling the electrosurgical instrument in pistol-like fashion to a generally aligned orientation for handling the electrosurgical instrument like a pencil.

While several embodiments of the electrosurgical instrument described above show an internally mounted cylinder 100 that fits within receptacle 25 of housing 11, it is envisioned that a portable gas supply may be used to accomplish the same purpose.

Referring now to FIG. 4, an alternative embodiment of the gas-enhanced surgical instrument is shown. In this embodiment, a portable gas supply is provided in a remote actuator assembly 550, here a foot actuator assembly used by the surgeon. However, the remote actuator assembly could be a hand operated actuator that is used by another person attending the surgical procedure, such as a nurse.

The surgical instrument 500 in this embodiment includes a hand-held applicator 510 and actuator assembly 550. The hand-held applicator 510 includes a frame, shown as an elongated housing 514, having a proximal end 516, a distal end 518 and an elongated cavity 520 extending therethrough. Distal end 518 of housing 514 includes a distal port 522 which is designed to emit, expel or disperse gas emanating from an elongated gas delivery member (here a channel or tube) 524 that in this embodiment runs generally longitudinally through frame or housing 514 of applicator 510. Tube 524 extends from the proximal end 516 of housing 514 for connection to supply tube 552 connected to actuator assembly 550. Tube 524 is for supplying pressurized gas 50 to the proximity of an active electrode 350 located adjacent distal end 518 of housing 514. Electrode 350 is proximal of port 522 such that the gas that is emitted from port 522 is ionized. At the other end of the housing 514, i.e., its proximal end 12, a connector 517 is provided so that hand-held applicator 510 can be connected to the actuator assembly 550 and, for example, a source of electrosurgical energy, such as electrosurgical generator 300, via electrical cable 575. A further description of the electrode and other components of the electrical system of or associated with the electrosurgical instrument of the present disclosure is provided below.

In the embodiment of FIG. 4, active electrode 350 can be attached to or mechanically engaged with the distal end of the housing and positioned adjacent to or at an operating site 410. Electrode 350 is positioned adjacent the distal end of frame or housing 514 between the distal end 525 of tube 524 and distal port 522, although the electrode can be located just to the exterior of port 522. For example, electrode 350 can be mounted to an elongated member that is supported within housing 514 and that extends outside of the housing, such that the electrode is positioned just outside of the port. Like the embodiment of FIG. 1, electrode 350 need not be as shown. It can be a conductive elongated member in the form of a blade, needle, snare or ball electrode that extends from an electrosurgical instrument and that is suitable, for example, for fulguration, i.e., coagulation, cutting or sealing tissue.

As shown and in most monopolar electrosurgical systems, a return electrode or pad 370 is typically positioned under the patient and connected to a different electrical potential on electrosurgical generator 300 via cable 360. During activation, return pad 370 acts as an electrical return for the electrosurgical energy emanating from hand-held applicator 510. It is envisioned that various types of electrosurgical generators 300 may be employed for this purpose, such as those generators sold by Valleylab, Inc.—a division of Tyco Healthcare Group LP, of Boulder, Colo.

It is envisioned that distal port 522 or distal end 518 of applicator 510 may be configured to facilitate or promote the dispersion of the ionized gas plasma 50' from distal port 522 in a uniform and consistent manner. For example, the distal end 518 may be tapered on one or all sides to direct the ionized plasma 50' toward the surgical or operative site 410. Alternatively, distal port 522 may be configured to disrupt or aggravate the dispersion or flow of gas plasma 50' exiting distal port 522 to enhance coagulation by creating a more turbulent gas flow. It is contemplated that many suitable devices, e.g., screws, fans, blades, helical patterns, etc., may be employed to cause gas plasma 50' to flow more or less turbulently or with other predetermined flow characteristics through tube 524 and/or out of distal port 522.

Although shown as a pencil-like hand-held applicator in the drawings, it is envisioned that the hand-held applicator may include a pistol grip-like handle which enables the user to handle the applicator like a pistol. The handle may be selectively pivotable for handling the hand-held applicator in different orientations, e.g., from an offset position relative to the housing for handling the applicator in pistol-like fashion to a generally aligned orientation for handling the applicator like a pencil.

Figure 5:
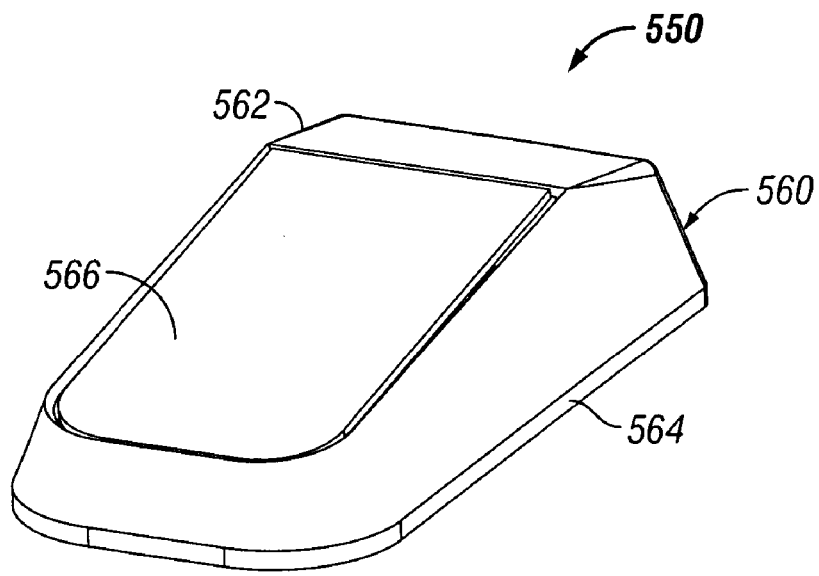
FIGS. 5-5B are perspective, side and frontal views of one embodiment of the actuator assembly of FIG. 4.
Figure 5A:
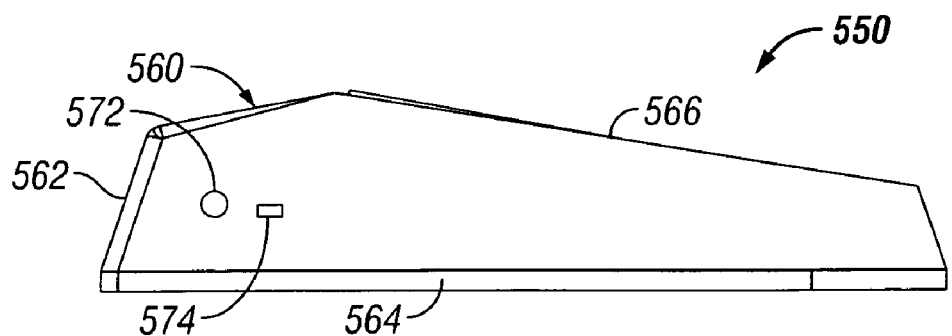
Figure 5B:
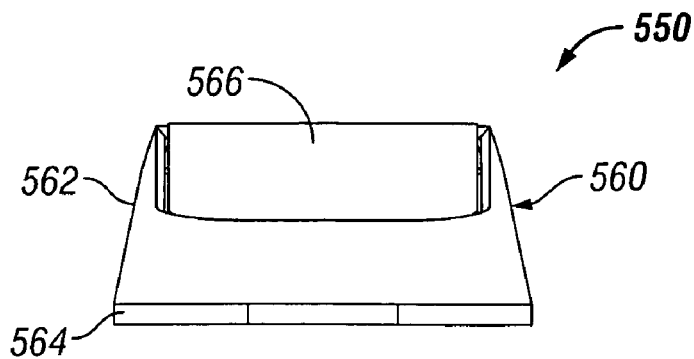
Figure 6:
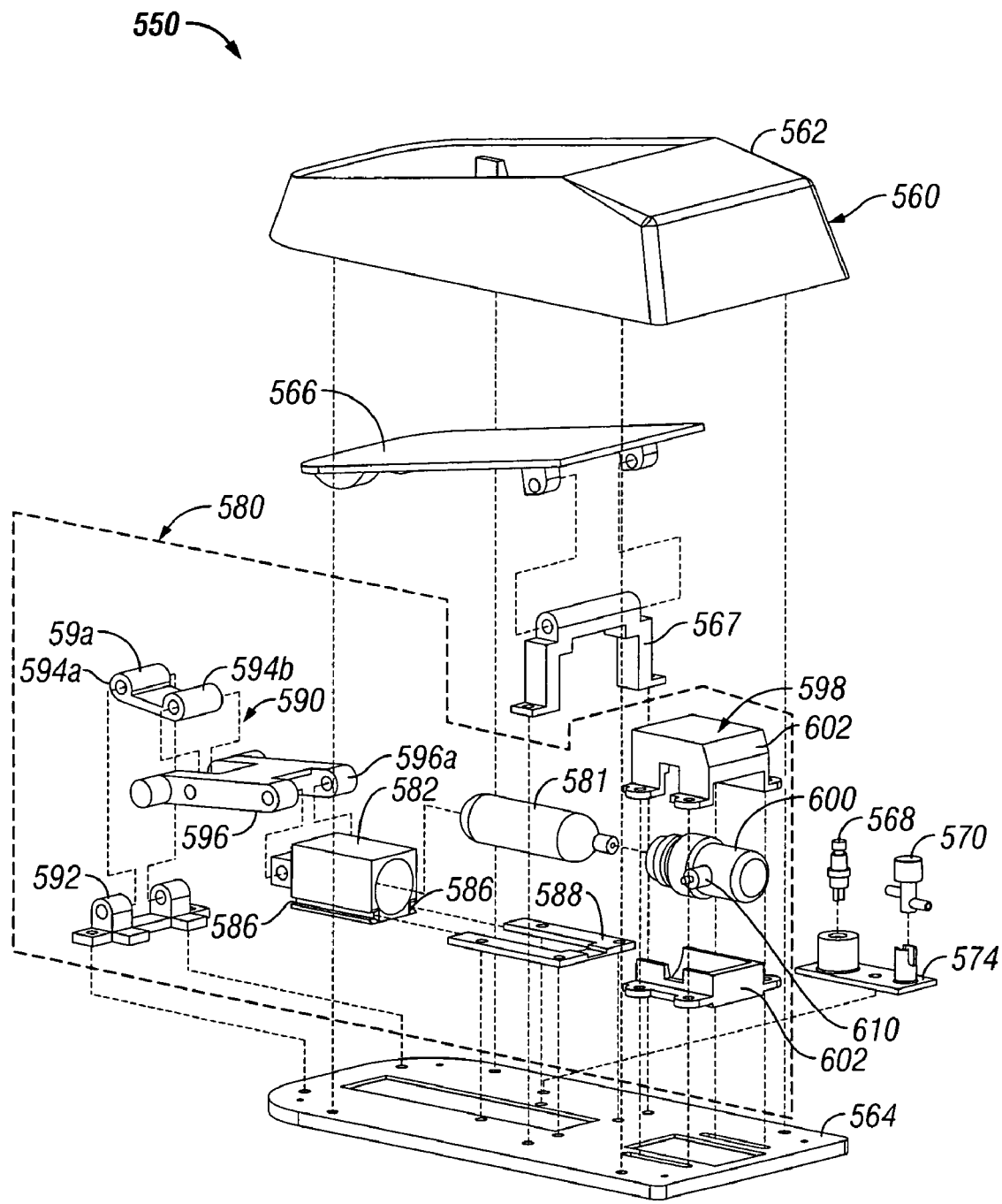
FIGS. 6 and 6A are perspective views with parts separated of the actuator assembly of FIG. 5.

Referring now to FIGS. 5-7 one embodiment of the actuator assembly 550 will be described. The actuator assembly 550 includes a housing 560 having a cover 562 connected to base 564. Cover 562 has an actuator 566, which in this embodiment is a foot pedal pivotably secured to bracket 567 (See FIG. 6), used to actuate one or more controllers and to puncture the outlet of the gas supply. In the embodiment of FIG. 4, there are two controllers, one used to control the gas supplied to applicator 510 and the other used to control the electrosurgical energy supplied to applicator 510.

Figure 6A:
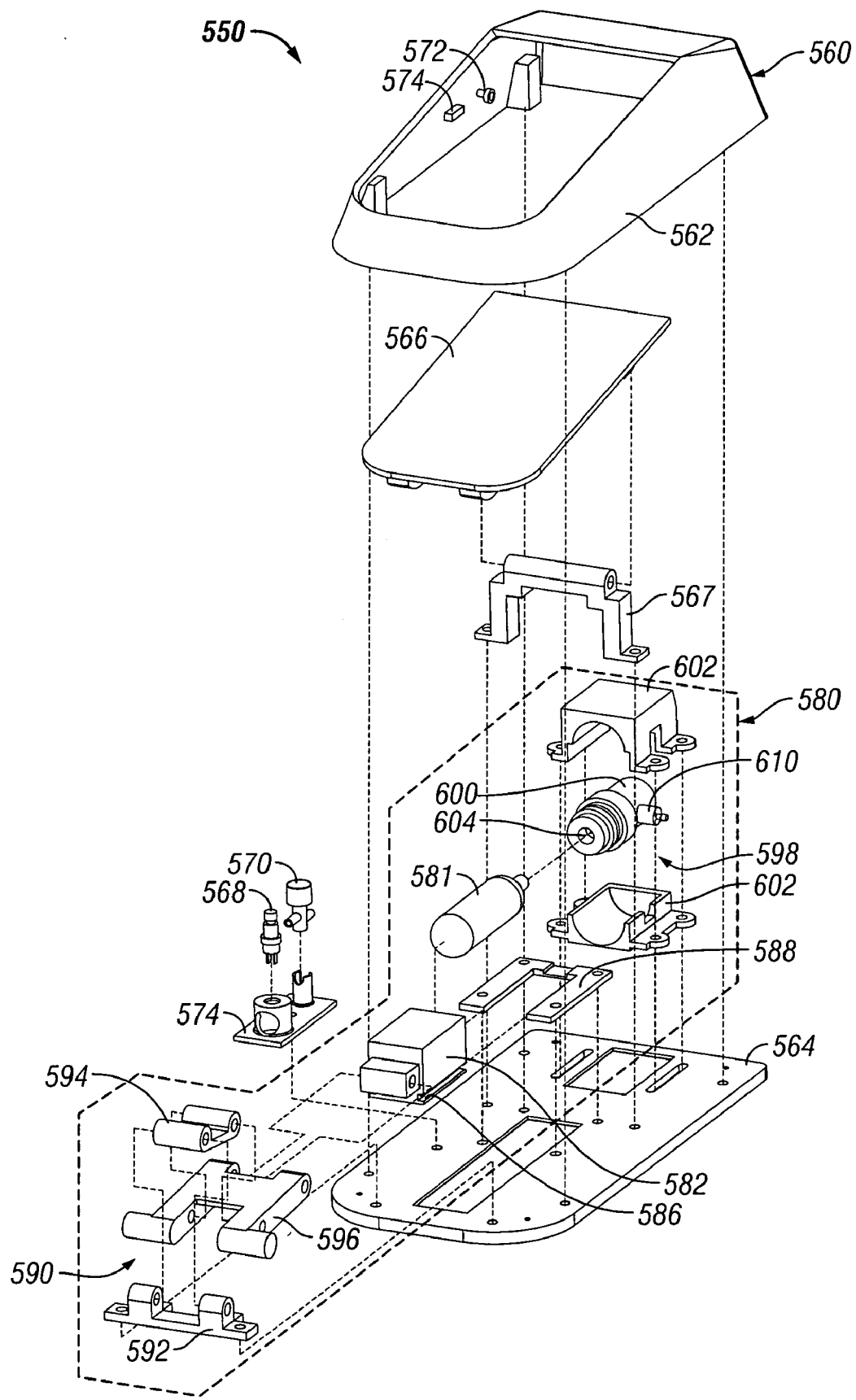

Referring to FIGS. 6 and 6A the two controllers 568 and 570 are secured to a mounting plate 572 which, in turn, is secured to base 564. Actuation of controller 568 is designed to energize electrode 350 in a simple "on/off" manner, e.g., when the controller is actuated (e.g., depressed or otherwise moved or manipulated) electrosurgical energy is supplied to the electrode 350. Actuation of controller 570 is designed to allow gas to flow from actuator assembly 550 to applicator 510 (See FIG. 6) for discharge to the operative site 410. Controller 570 is preferably an open and close type valve that permits or blocks the flow of the pressurized gas. When using this type of controller 570 the pressure of the gas in the cylinder 581 is the pressure of the gas supplied to applicator 510. Alternatively, controller 570 may be a regulator/valve assembly that selectively controls and/or regulates the flow of gas from cylinder 581 to applicator 510. It is also envisioned that controller 570 may be an adjustable valve that controls the flow of pressurized gas with a rotatable knob, slidable lever or pressure sensitive pad extending from housing 560. The controller 570 may also provide the user with tactile or audible feedback that is indicative of the flow of gas.

Housing 560 also houses a gas source module 580 that holds a portable source of pressurized ionizable gas for the surgical procedure being performed. Gas source module 580 includes a receptacle 582 configured to securely engage, receive, seat or otherwise hold a source of pressurized ionizable gas and to move the gas source between a disengaged position shown in FIG. 10 and an engaged position shown in FIG. 11. The gas source shown is a cylinder 581 containing pressurized ionizable gas. However, other types of portable containers, canisters, cartridges and the like are also contemplated. The cylinder 581 shown is similar to the cylinders 100, 100', 100" and 100'" described above. However, since the actuator assembly 550 may be larger than the applicator 510, larger or longer pressurized containers, canisters, cylinders or cartridges may be employed to provide more pressurized gas during prolonged use. Details of the engagement of cylinder 581 in the actuator assembly 550 are discussed in more detail below with reference to FIGS. 8-18.

Referring to FIG. 7, receptacle 582 includes a pair of groves 586 that fit onto rail 588 secured to base 564 so that cylinder 581 is movable between the disengaged and engaged positions. A gas source locking assembly 590 is provided to facilitate movement of receptacle 582 and to lock the receptacle in place when the cylinder 581 is in the engaged position so as to maintain sufficient pressure on the receptacle 582 (and thus the cylinder 581) to ensure that the outlet of the cylinder is sealed in coupler assembly 598 and pressurized gas is prevented from leaking into the housing. Locking assembly 590 includes pivot arm mount 592 secured to base 564, pivot arm 594 pivotably secured at one end 594a to mount 592 and pivotably secured to locking arm 596 at end 594b. End 596a of locking arm 596 is pivotably secured to receptacle 582 as shown.

Figure 7B:
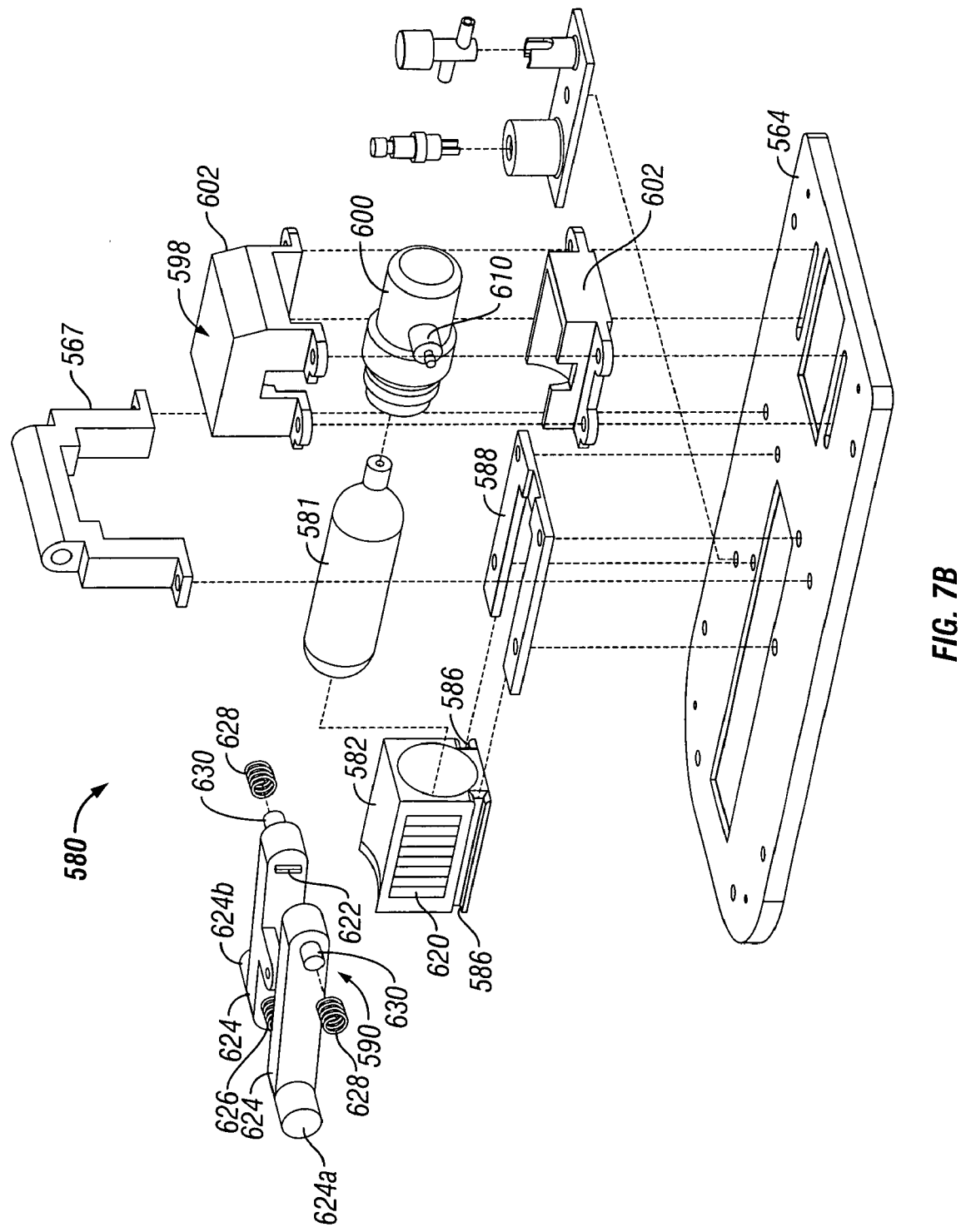
FIG. 7B is a perspective view with parts separated of another embodiment of the gas source module in the actuator assembly.

Alternatively, as seen in FIG. 7B, the locking assembly 590 may be a ratchet mechanism where receptacle 582 includes a series of grooves 620 on one or both sides and one or more teeth 622 configured to engage the groves 620 and lock the receptacle in position are provided on pivotable arms 624. Spring 626 normally biases ends 624a of arms 624 away from each other so that the teeth 622 move toward each other. Springs 628 supported by pins 630 on arms 624 engage inner walls of the housing 560 and assist spring 626 in normally biasing the teeth 622 toward each other. To release the teeth 622 from grooves 620, ends 624a of arms 624, which partially extend outside from housing 560 are manually pressed or crimped so that springs 626 and 628 are compressed and ends 624b of arms 624 spread apart.

The gas source module 580 also includes a coupler assembly 598 configured to engage the outlet of the cylinder 581 and provide a hermetic seal around the outlet of the cylinder so that gas does not escape from the coupler assembly. Coupler assembly 598 includes a coupler 600 secured within housing 602 secured to base 564. Coupler 600 may be constructed of an elastomeric material so that when the outlet of cylinder 581 is pressed into port 604 (seen in FIG. 7A) of coupler 600 a hermetic seal forms around the outlet of the cylinder. The interior of port 604 has a pin 606 used to break, rupture or puncture the seal on the outlet when a new cylinder is first moved to the engaged position as will be described below. Coupler 600 also has a channel 608 and an exit port 610 that connects to tube 612 connected to controller 570 (seen in FIG. 12).

It is also contemplated that actuator assembly 550 (or generator 300) may cooperate with one or more sensors 365 that can be attached to housing 514 of applicator 510 or electrode 350 (seen in FIG. 4). Like the sensors described above with respect to the embodiment of FIG. 1, sensors 365 can be used to continually measure or monitor a condition at the operative site 410, e.g., the amount of tissue coagulation, and relay the information back to generator 300 or actuator assembly 550. For example, a control system or safety circuit (not shown) may be employed to automatically (e.g., through a shut-off switch) reduce gas pressure or partially actuate controller 570 of actuator assembly 550 if an obstruction is detected. Alternatively or in addition, the safety circuit may be configured to cut off the electrosurgical energy to tissue 400 (via electrode 350) and/or activate or release a pressure relief valve (e.g., a safety release valve generally designated 367) to change the pressure of the gas discharged from the distal end 522 of the applicator 510 in response to a condition (e.g., an embolic condition or concern) sensed by sensor 365 or by the surgeon. For example, during operation, pressure release valve 367 may be depressed or rotated into housing 514 to constrict supply tube 524 and reduce the volume of gas discharged from the distal end 522 of applicator 510.

It is also envisioned that based upon the sensed condition, controller 570 may be automatically deactivated or closed. Alternatively, sensor 365 may provide feedback to actuator assembly 550 or generator 300 to optimize performance of the surgical function, here coagulation of the tissue 400, based upon, for example, 1) the distance of the applicator 510 from the tissue deduced from the measured back pressure in supply tube 524, 2) tissue type, or 3) tissue response. A second sensor 321 may be employed to measure the flow of gas 50 through gas supply tube 524, and may be electrically connected to a flow regulator (not shown) to automatically regulate the flow of gas from cylinder 581 to electrode 350.

Figure 8:
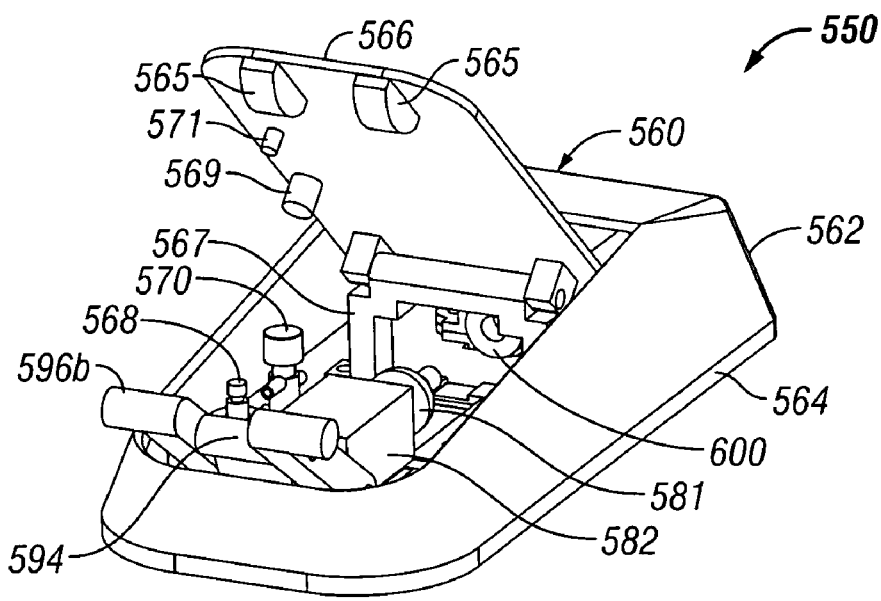
FIG. 8 is a perspective view of the actuator assembly of FIG. 5, with a foot pedal in an open position and showing the gas source module with a portable gas source in a disengaged position.
Figure 9:
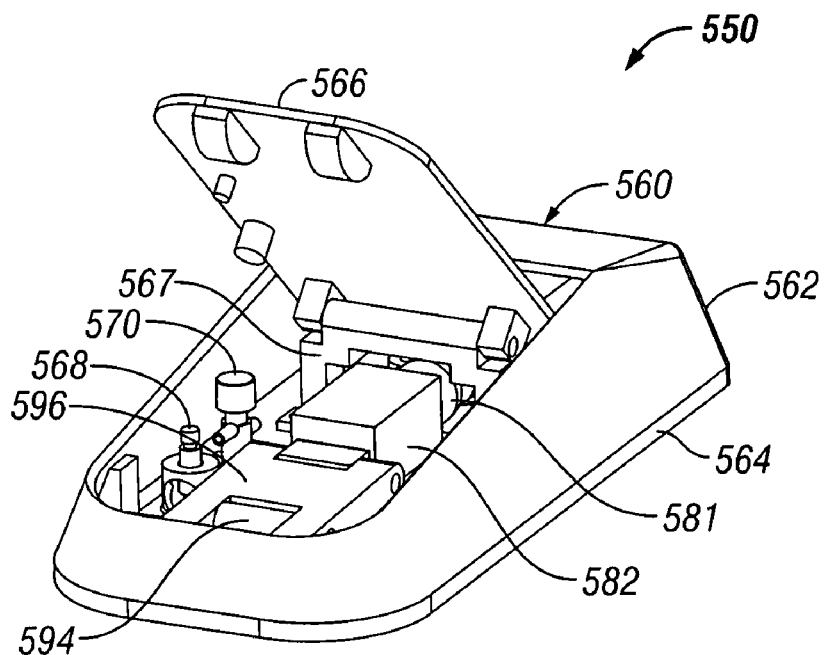
FIG. 9 is a perspective view of the actuator assembly of FIG. 5, with the foot pedal in the open position and showing the gas source module with the portable gas source in an engaged position.
Figure 10:
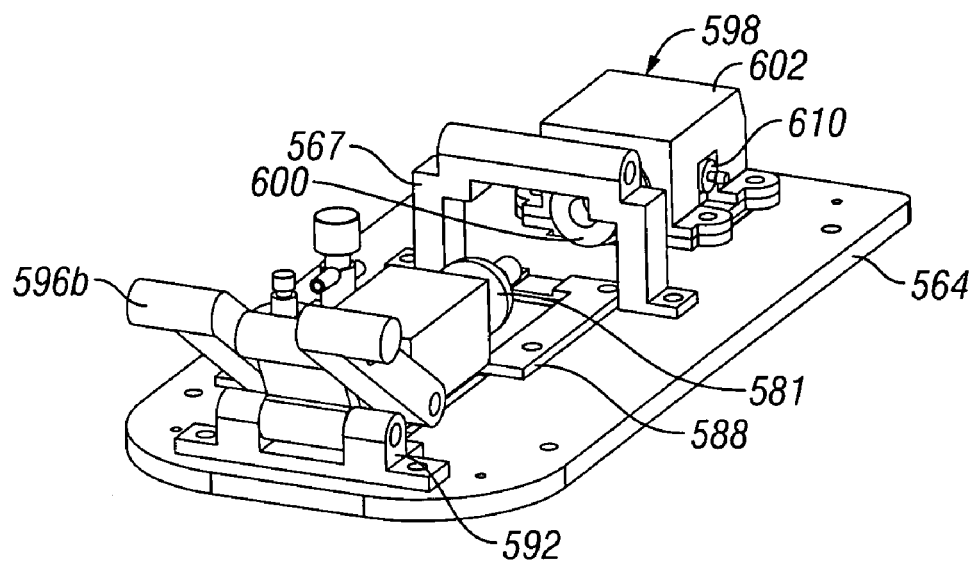
FIG. 10 is a perspective view of the interior of the actuator assembly of FIG. 8, showing the gas source module with a portable gas source locking assembly and the gas source in the disengaged position.

Referring now to FIGS. 8-18 the operation of the applicator 510 and actuator assembly 550 to supply ionized gas to the operative site 410 will be described. Prior to or at the beginning of the surgical procedure the actuator 566 is lifted (seen in FIG. 8) and a sealed portable source of pressurized ionizable gas, e.g. cylinder 581, is inserted into receptacle 582 of gas source module 580. As shown in FIGS. 8 and 10, when inserting a cylinder the gas source module 580 is in a retracted position where the outlet of the cylinder 581 is not engaged with coupler 600 of coupler assembly 598. Generally, when in the disengaged position, locking arm 596 of locking assembly 590 is in a retracted position (seen in FIGS. 14 and 16) so that end 596b of the locking arm extends from housing 560 and receptacle 582 is retracted along rail 588 so that the outlet of cylinder 581 is positioned away from coupler 600. After the cylinder 581 is placed in the receptacle 582, end 596b of locking arm 596 is pushed, preferably in the direction of arrow A (seen in FIG. 16), so that receptacle 582 slides along rail 588 in the direction of arrow B (seen in FIG. 17) towards coupler assembly 598 and the outlet of cylinder 581 enters port 604 of coupler 600. At this point, actuator 566 can pivot to a closed position (seen in FIG. 18).

Figure 11:
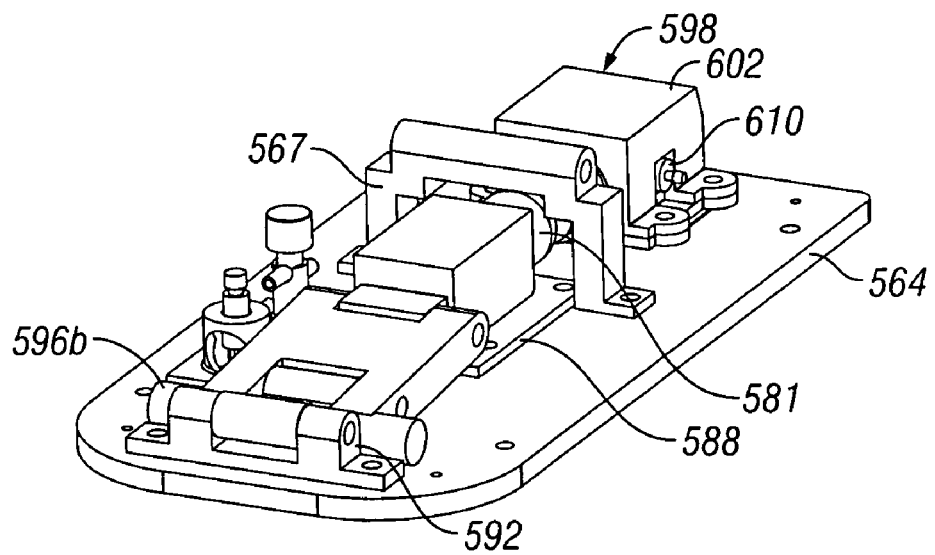
FIG. 11 is a perspective view of the interior of the actuator assembly of FIG. 9, showing the gas source module with the portable gas supply is in the engaged position and the portable gas source locking assembly locked.

To supply ionized gas to the operative site 410 after a cylinder is first inserted into the receptacle 582, the seal on the sealed portable source of pressurized ionizable gas, e.g., cylinder 581, needs to be opened. To puncture (or open) the seal on the outlet of cylinder 581, the user firsts applies sufficient pressure to actuator 566 so that pressure pads 565 attached to actuator 566 engage end 596b of locking arm 596 causing the receptacle to further move along rail 588 so that the outlet of cylinder 581 is pressed against pin 606 in coupler 600 to puncture the seal. When the cylinder seal is punctured, end 596b of locking arm 596 rests against mount 592, as shown in FIG. 11, so that the outlet of cylinder 581 is sealed within coupler 600.

Figure 12:
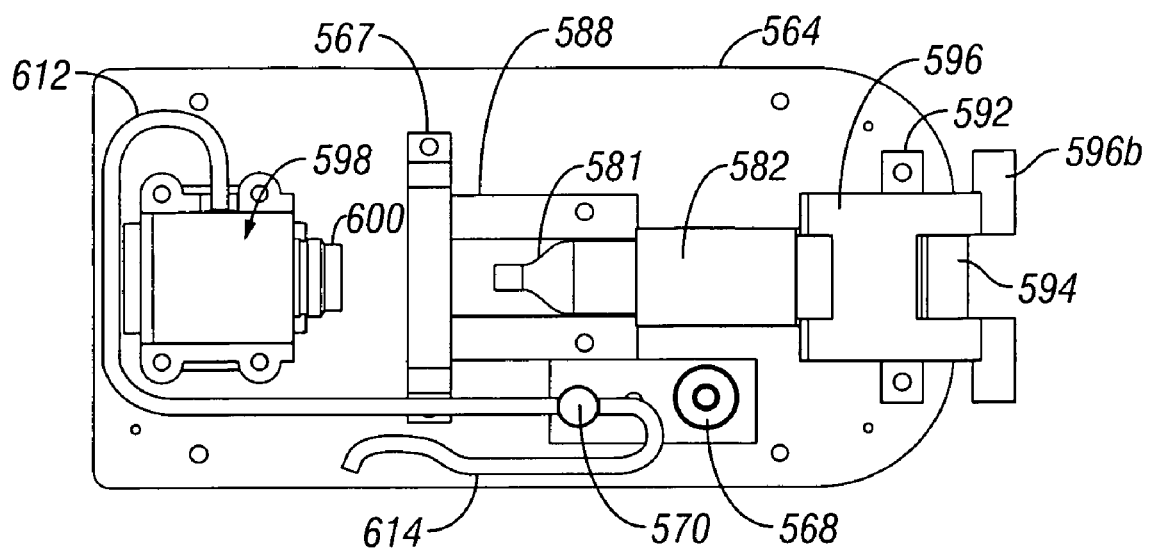
FIG. 12 is a top view of the interior of the actuator assembly of FIG. 10, showing a coupler assembly and corresponding portable gas supply in the disengaged position relative to the coupler assembly.
Figure 13:
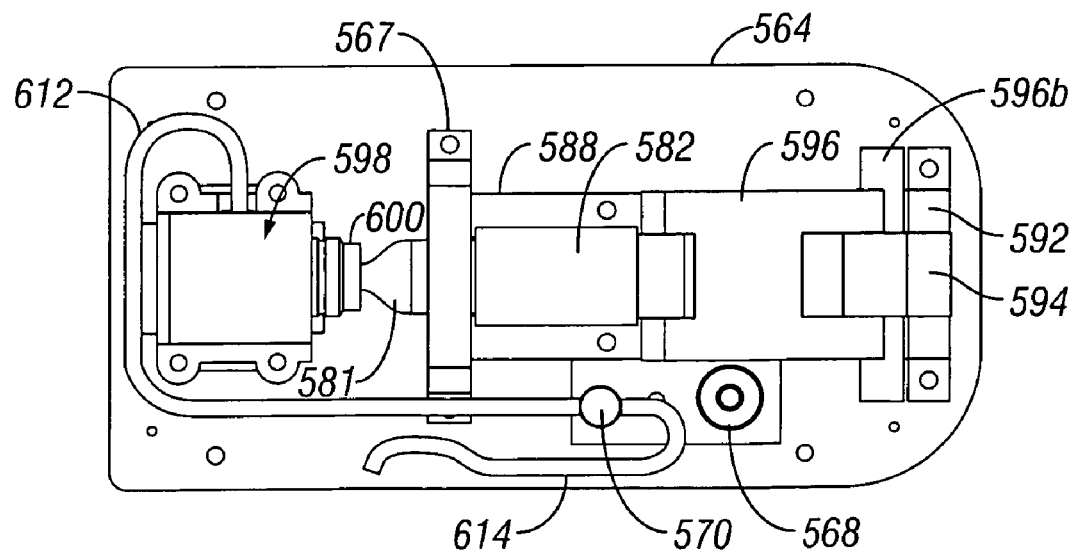
FIG. 13 is a top view of the interior of the actuator assembly of FIG. 11, showing the coupler assembly and corresponding portable gas supply in the engaged position relative to the coupler assembly.
Figure 14:
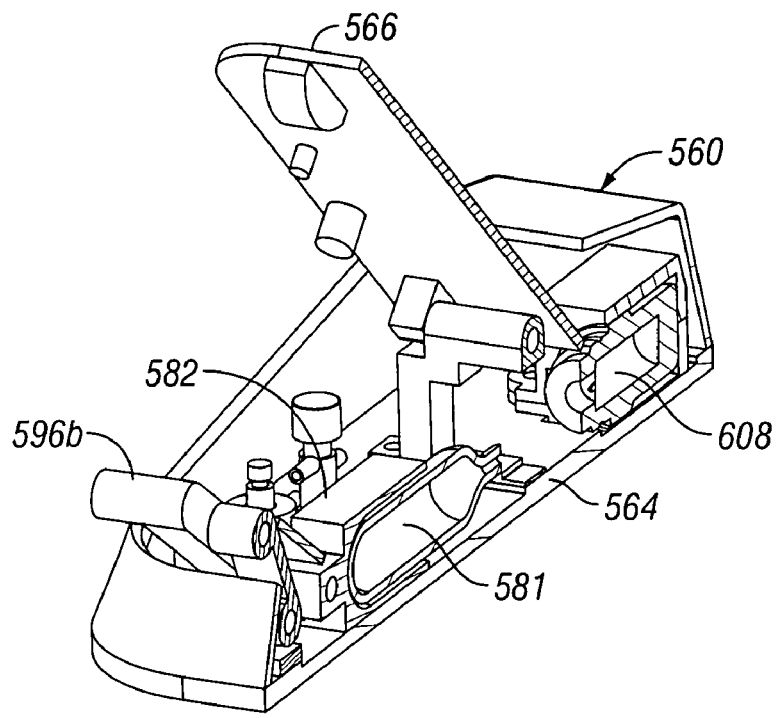
FIG. 14 is a perspective view of a cross-section of the actuator assembly of FIG. 5, showing the foot pedal in the open position and the gas source module in the disengaged position.
Figure 15:
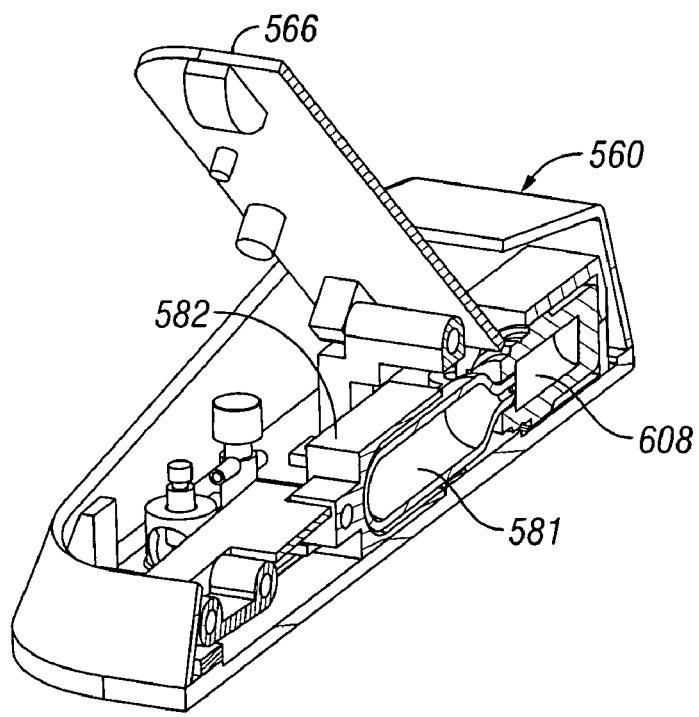
FIG. 15 is a perspective view of a cross-section of the actuator assembly similar to FIG. 14, showing the foot pedal in the open position and the gas source module in the engaged position.
Figure 16:
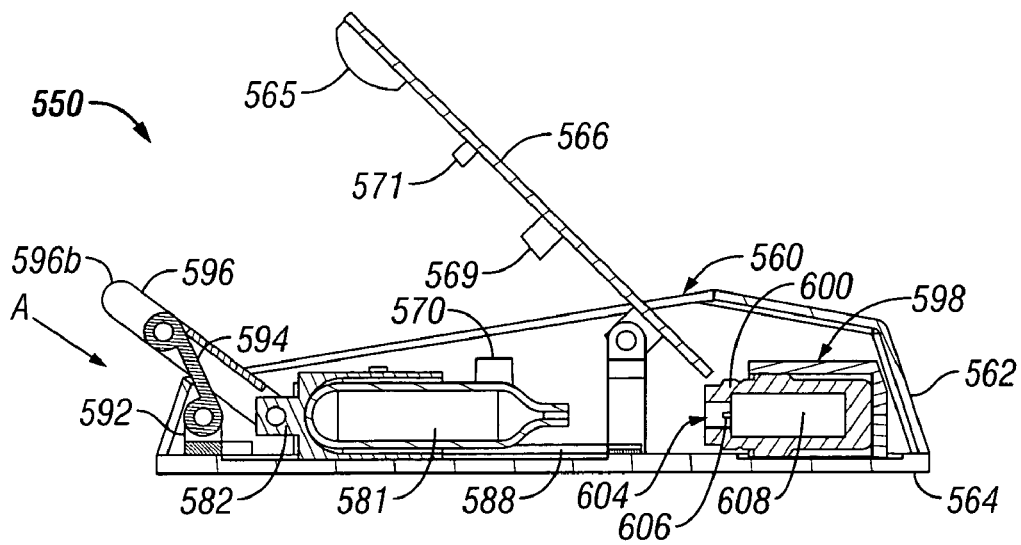
FIG. 16 is a side cross-sectional view of the actuator assembly of FIG. 5, showing the foot pedal in the open position and the gas source module in the disengaged position.
Figure 17:
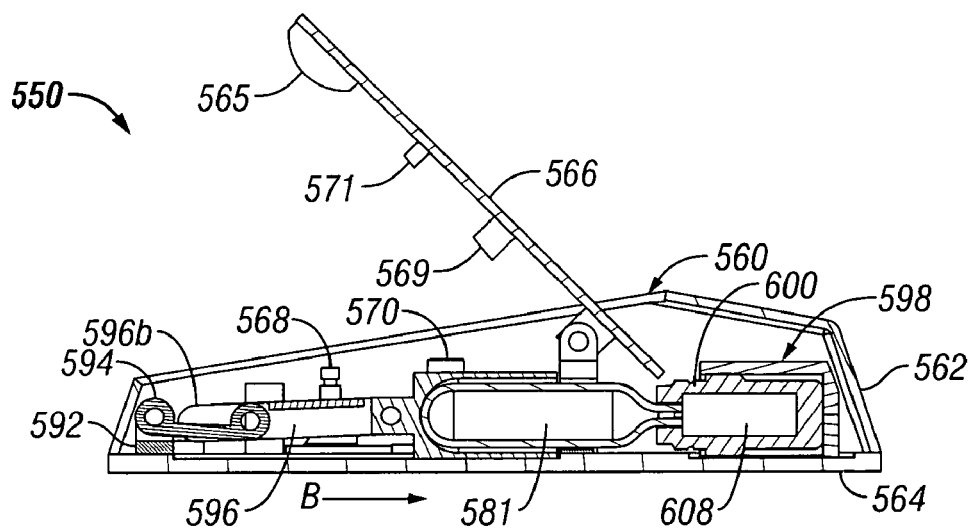
FIG. 17 is a side cross-sectional view of the actuator assembly of FIG. 5, showing the foot pedal in the open position and the gas source module in the engaged position.
Figure 18:
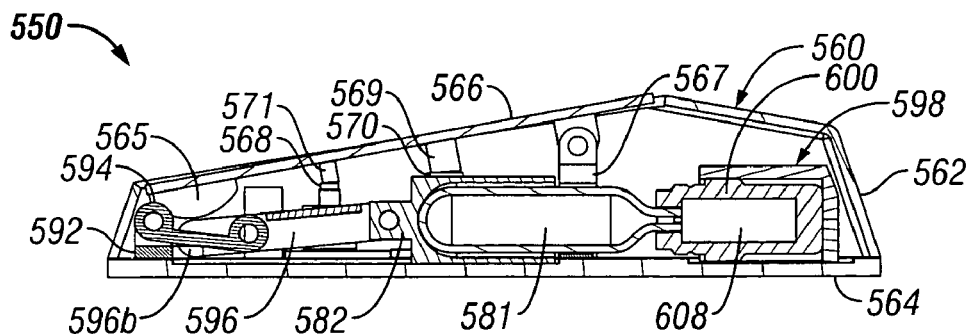
FIG. 18 is a side cross-sectional view of the actuator assembly of FIG. 5, showing the foot pedal in a closed position and pads attached to the foot pedal used to actuate gas supply and energy controllers.

Once the seal in the cylinder is punctured pressurized gas passes through channel 608 in coupler 600 and exits the coupler via exit port 610 (See FIGS. 10-13). Pressurized gas then passes through tube 612 to controller 570. As pressure is being applied by the user to puncture the sealed cylinder, pad 569 attached to actuator 566 engages controller 570 (as seen in FIGS. 12 and 18) and actuates the controller causing pressurized gas to flow through tube 614 to port 572 in housing 562 and exit the actuator assembly 550. Similarly, pad 571 attached to actuator 566 engages controller 568 (as seen in FIG. 18) and actuates the controller causing energy to flow from connector 574 to the electrode 350 in the applicator 510. Connector 574 is a conventional electrical connector used to electrically connect the actuator assembly 550 to the cable 575.

It should be noted that pads 569 and 571 can be dimensioned such that a first level of pressure causes pad 569 to actuate controller 570 and a second level of pressure causes pad 571 to actuate controller 568 so that pressurized gas is provided to applicator 510 prior to electrosurgical energy being supplied to electrode 350. Alternatively, pads 569 and 571 can be dimensioned so that pressurized gas and electrosurgical energy are supplied to the applicator 510 at the same time. To actuate controllers 568 and 570 after the cylinder 581 seal is initially punctured the user need only apply sufficient pressure to actuator 566 to cause actuation of the controllers as described above.

Referring now to FIG. 19, an alternative embodiment of the applicator 510' and actuator assembly 550' is shown. In this embodiment, the actuator assembly 550' includes the controller 570 for controlling the flow of pressurized gas to the applicator 510', and the hand-held applicator includes the controller 568 that controls the energy supplied to the electrode 350. As a result the cable 575 between the applicator 510' and the actuator assembly 550' is not needed and the electrical connections for this embodiment are similar to those described above with respect to FIG. 1. Operation of the actuator assembly is similar to the operation described above, except for the description of controller 568 which is not included in this embodiment. During a surgical procedure using this embodiment of the electrosurgical instrument pressurized gas is provided upon actuation of the controller 570 in actuator assembly 550' and electrosurgical energy is supplied to the electrode upon actuation of controller 568 in hand-held applicator 510'.

As can be appreciated, use of a remote actuator assembly would allow the use of a larger gas supply than in the frame or handle of a hand-held instrument, thus reducing the number of times that the user would have to replace the gas supply during prolonged use. Further, the gas supply hose 552 may be attached to the electrosurgical cable 575 which attaches to the proximal end of the applicator 510 to limit tangling.

It is envisioned that the electrosurgical instrument (i.e., the applicator and actuator assembly) and the source of pressurized ionizable gas (e.g., cylinder 581) may be completely disposable or the electrosurgical instrument may be reposable and the gas source disposable. Moreover, the mechanically engaging end of the gas source may be designed for easy retrofit onto exiting electrosurgical instruments. It is also envisioned that the applicator 510 and/or 510' can include a second flow regulator (not shown) to regulate the flow of pressurized gas to electrode 350.

Moreover, as noted above, although it is preferable to utilize argon as the ionizable gas for promulgating coagulation of the tissue, in some cases it may be preferable to use another ionizable gas or a combination of ionizable gases to effect the same or a similar or different result.

There have been described and illustrated herein several embodiments of a gas enhanced electrosurgical instrument for arresting bleeding and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrosurgical instrument for providing pressurized ionized gas to a surgical site, comprising:
    a hand-held applicator having proximal and distal ends, a gas delivery member adapted to deliver pressurized ionizable gas to the proximity of an electrode located adjacent the distal end of the applicator, the electrode being adaptable to connect to a source of electrosurgical energy; and
    a portable actuator assembly configured to selectively store a source of pressurized ionizable gas therein, the portable actuator assembly including a housing having an actuator pivotably secured to the housing and at least one controller located within the housing and coupled to the source of pressurized ionizable gas that controls the delivery of the gas from the supply of pressurized ionizable gas to the hand-held applicator and controls the delivery of electrosurgical energy to the hand-held applicator, wherein the housing actuator is configured to engage the at least one controller upon actuation; and
    wherein upon actuation of the at least one controller by the housing actuator, gas from the source of pressurized ionizable gas is delivered to the proximity of the electrode though the gas delivery member and electrosurgical energy is delivered to the electrode, such that an ionized gas is emitted from the distal end of the hand-held applicator.

2. The electrosurgical instrument according to claim 1, wherein the hand-held applicator comprises a tubular frame having a proximal end and a distal end, the distal end having a port defined therein for emitting the ionized gas.

3. The electrosurgical instrument according to claim 2, wherein the gas delivery member comprises a tube extending through the tubular frame.

4. The electrosurgical instrument according to claim 1, wherein the at least one controller is adapted to cause delivery of gas from the source of pressurized ionizable gas to the hand-held applicator prior to causing the delivery of the electrosurgical energy to the hand-held applicator.

5. The electrosurgical instrument according to claim 1, wherein the at least one controller comprises a first controller that controls the flow of gas from the source of pressurized ionizable gas to the hand-held applicator, and a second controller that controls delivery of the electrosurgical energy to the to the electrode.

6. The electrosurgical instrument according to claim 5, wherein the first controller causes the flow of gas from the source of pressurized ionizable gas to the hand-held applicator prior to the second controller causing the delivery of the electrosurgical energy to the hand-held applicator.

7. The electrosurgical instrument according to claim 5, wherein the first controller includes a valve and the second controller includes a switch.

8. The electrosurgical instrument according to claim 7, wherein the valve is actuated prior to actuation of the switch.

9. The electrosurgical instrument according to claim 1, wherein the source of pressurized ionizable gas includes a cylinder containing pressurized ionizable gas.

10. The electrosurgical instrument according to claim 9, wherein the gas in the cylinder comprises argon.

11. The electrosurgical instrument according to claim 1, wherein the source of pressurized ionizable gas includes a cartridge containing pressurized ionizable gas.

12. The electrosurgical instrument according to claim 11, wherein the gas in the cartridge comprises argon.

13. The electrosurgical instrument according to claim 1, wherein the portable actuator assembly comprises:
    a gas source module within the housing for holding the source of pressurized ionizable gas.

14. The electrosurgical instrument according to claim 13, wherein the portable actuator assembly comprises:
    a second controller located within the housing and connectable to a source of electrosurgical energy such that actuation of the second controller by the housing actuator causes the delivery of electrosurgical energy to the hand-held applicator.

15. The electrosurgical instrument according to claim 13, wherein the gas source module comprises:
    a receptacle configured to hold the source of pressurized ionizable gas and movable so that the source of pressurized ionizable gas is movable between engaged and disengaged positions;
    a locking assembly for locking the receptacle when the source of pressurized ionizable gas is in the engaged position; and
    a coupler assembly in communication with the at least one controller and configured to engage at least a portion of the source of pressurized ionizable gas so that gas from the source is provided to the at least one controller.

16. The electrosurgical instrument according to claim 15, wherein the source of pressurized ionizable gas comprises a cylinder containing pressurized ionizable gas.

17. The electrosurgical instrument according to claim 16, wherein the cylinder includes a sealed outlet and the coupler assembly is configured to rupture the sealed outlet when the cylinder is moved to the engaged position.

18. The electrosurgical instrument according to claim 16, wherein the gas contained in the cylinder is argon.

19. The electrosurgical instrument according to claim 15, wherein the source of pressurized ionizable gas comprises a cartridge containing pressurized ionizable gas.

20. The electrosurgical instrument according to claim 19, wherein the gas contained in the cartridge is argon.

21. The electrosurgical instrument according to claim 19, wherein the cartridge includes a sealed outlet and the coupler assembly is configured to rupture the sealed outlet when the cartridge is moved to the engaged position.

22. The electrosurgical instrument according to claim 1, wherein the electrosurgical instrument is configured to coagulate body tissue.

23. The electrosurgical instrument according to claim 1, wherein the electrosurgical instrument is configured and adapted for use in an endoscopic application.

24. The electrosurgical instrument according to claim 1, wherein the ionizable gas comprises a mixture of inert gases.

25. The electrosurgical instrument according to claim 1, wherein the source of pressurized ionizable gas is visibly coded to indicate a characteristic of at least one of the type of gas in the supply of pressurized ionizable gas and the pressure of the pressurized ionizable gas.

* * * * *